US010912251B2

(12) United States Patent
Pickett et al.

(10) Patent No.: US 10,912,251 B2
(45) Date of Patent: Feb. 9, 2021

(54) METHOD FOR TREATING PLANTS WITH RESPECT TO ESTIMATED ROOT ZONES

(71) Applicant: Deere & Company, Moline, IL (US)

(72) Inventors: Terence D. Pickett, Waukee, IA (US); Richard J. Connell, Slater, IA (US); Larry L. Hendrickson, Grimes, IA (US); Frederick W. Nelson, Waukee, IA (US); Brandon M. McDonald, Johnston, IA (US); Noel W. Anderson, Fargo, ND (US)

(73) Assignee: DEERE & COMPANY, Moline, IL (US)

( * ) Notice: Subject to any disclaimer, the term of this patent is extended or adjusted under 35 U.S.C. 154(b) by 222 days.

(21) Appl. No.: 16/023,438

(22) Filed: Jun. 29, 2018

(65) Prior Publication Data

US 2019/0124826 A1 May 2, 2019

Related U.S. Application Data

(60) Provisional application No. 62/579,823, filed on Oct. 31, 2017.

(51) Int. Cl.
*A01C 21/00* (2006.01)
*A01M 7/00* (2006.01)
(Continued)

(52) U.S. Cl.
CPC .......... *A01C 21/007* (2013.01); *A01C 21/002* (2013.01); *A01C 23/02* (2013.01);
(Continued)

(58) Field of Classification Search
CPC ...... A01C 21/007; A01G 25/16; G01N 33/24; A01M 7/0089
See application file for complete search history.

(56) References Cited

U.S. PATENT DOCUMENTS 4,699,220 A * 10/1987 Strohm .................. A01B 13/08
172/160
5,279,068 A 1/1994 Rees et al.
(Continued)

FOREIGN PATENT DOCUMENTS

CA 1178850 A 12/1984
CN 106035294 A 10/2016
(Continued)

OTHER PUBLICATIONS

McWilliams, Corn Growth and Magement Quick Guide, North Dakota State University and University of Minnesota, Jun. (Year: 1999).*
(Continued)

*Primary Examiner* — Michael J Dalbo

(57) ABSTRACT

A method for treating plants comprises estimating a growth state or maturity state of a plant based on a planting date, a current date and the crop type of the plant. A root zone estimator or data processor estimating a size, diameter or radius of a root zone of the plant based on the determined growth state or maturity state. The data processor adjusts a lateral offset of a distribution pattern of a crop input or nutrient from at least one nutrient knife based on the size, diameter or radius of the root zone and safety zone about the root zone, where the at least one nutrient knife tracks a path outside of or bounded by the root zone.

26 Claims, 15 Drawing Sheets

(51) Int. Cl.
*A01C 23/02* (2006.01)
*G01N 33/24* (2006.01)

(52) U.S. Cl.
CPC ......... *A01M 7/0089* (2013.01); *A01C 23/023* (2013.01); *A01C 23/024* (2013.01); *A01M 7/0042* (2013.01); *G01N 33/24* (2013.01)

(56) References Cited

U.S. PATENT DOCUMENTS

| | | | |
|---|---|---|---|
| 5,613,635 | A | 3/1997 | Harden et al. |
| 5,668,719 | A | 9/1997 | Bobrov et al. |
| 6,216,387 | B1* | 4/2001 | Stoller ................. A01G 29/00 47/48.5 |
| 6,393,927 | B1 | 5/2002 | Biggs et al. |
| 6,442,486 | B1 | 8/2002 | Satake et al. |
| 9,320,196 | B2 | 4/2016 | Dybro et al. |
| 9,336,584 | B2 | 5/2016 | Ulman |
| 9,652,840 | B1 | 5/2017 | Shriver et al. |
| 2008/0046130 | A1 | 2/2008 | Faivre et al. |
| 2009/0321537 | A1 | 12/2009 | Nelson et al. |
| 2012/0215410 | A1 | 8/2012 | McClure et al. |
| 2013/0105591 | A1 | 5/2013 | Peterson |
| 2013/0145805 | A1* | 6/2013 | Olson ...................... C05G 3/70 71/6 |
| 2014/0230391 | A1 | 8/2014 | Hendrickson et al. |
| 2015/0015697 | A1 | 1/2015 | Redden et al. |
| 2015/0027044 | A1 | 1/2015 | Redden |
| 2015/0254800 | A1 | 9/2015 | Johnson et al. |
| 2016/0084813 | A1 | 3/2016 | Anderson et al. |
| 2016/0368011 | A1 | 12/2016 | Feldhaus et al. |
| 2018/0189564 | A1* | 7/2018 | Freitag ................. A01G 22/00 |
| 2018/0199499 | A1* | 7/2018 | Adams ................. A01C 7/205 |

FOREIGN PATENT DOCUMENTS

| | | | |
|---|---|---|---|
| DE | 102011050877 | A1 | 9/2012 |
| EP | 0277108 | A2 | 8/1988 |
| EP | 2214476 | A1 | 8/2010 |
| WO | 2008153927 | A2 | 12/2008 |
| WO | 2016061672 | A1 | 4/2016 |
| WO | 2016154482 | A1 | 9/2016 |

OTHER PUBLICATIONS

Weigand, Multi-frequency electrical impedance tomography as a non-invasive tool to characterize and monitor crop root systems, Biogeosciences, 14, 921-939 (Year: 2017).*
Nutrient Application Parts Family. Parts catalog [online]. Deere & Company, 2012 [retrieved on May 9, 2018]. Retrieved from the Internet: <URL:https://jdparts.deere.com/partsmkt/document/english/pmac/42282_fb_NutrientApplicationPartsFamily.htm>.
2510H Nutrient Applicator. Product sheet [online]. Deere & Company, 2018 [retrieved on May 9, 2018]. Retrieved from the Internet: <URL: https://www.deere.com/en_US/products/equipment/nutrient_application/nutrient_applicators/2510h/2510h.page>.
Chad, Lee. "Corn Growth Stages and Growing Degree Days." University of Kentucky College of Agriculture, Lexington, KY. Sep. 2011 [online] [retrieved on May 9, 2018]. Retrieved from the Internet <URL: www2.ca.uky.edu/agc/pubs/agr/agr202/agr202.pdf>.
Nafziger, Emerson. "Corn" in Illinois Agronomy Handbook. College of Agricultural, Consumer, and Environmental Sciences, University of Illinois at Urbana Champaign, 2009 [online] [retrieved on May 9, 2018]. Retrieved from the Internet <URL:http://extension.cropsciences.illinois.edu/handbook/>.
A User's Guide to Spray Nozzles. Brochure [online]. TeeJet Technologies, 2013 [retrieved on May 9, 2018]. Retrieved from the Internet <URL: http://teejet.it/media/40076/user%27s%20guide%20to%20spray%20nozzles_2013_lo-res-sequential.pdf>.
Schumann, Arnold W. "Precise Placement and Variable Rate Fertilizer Application Technologies for Horticultural Crops." HortTechnology, vol. 20, Issue 1. Feb. 1, 2010, pp. 34-40.
Search Report issued in counterpart application No. EP18203210.2, dated Mar. 21, 2019 (8 pages).
Search Report issued in related application No. EP18203311.8, dated Apr. 16, 2019 (6 pages).

* cited by examiner

S801 — DETERMINE A GROWTH STATE OR MATURITY STATE OF A PLANT BASED ON A PLANTING DATE, A CURRENT DATE AND THE CROP TYPE OF THE PLANT.

S802 — ESTIMATE A SIZE OR RADIUS OF THE ROOT ZONE OF THE PLANT BASED ON THE DETERMINED GROWTH STATE.

S803 — ADJUST A LATERAL OFFSET OF A SPRAY PATTERN OF A NOZZLE BASED ON THE SIZE OR RADIUS TO TARGET ALIGNMENT OR MAXIMIZATION OF OVERLAP AREA OF A STRIP OF THE SPRAY PATTERN WITH THE CORRESPONDING ROOT ZONE.

FIG. 8

S801 — DETERMINE A GROWTH STATE OR MATURITY STATE OF A PLANT BASED ON A PLANTING DATE, A CURRENT DATE AND THE CROP TYPE OF THE PLANT.

S802 — ESTIMATE A SIZE OR RADIUS OF THE ROOT ZONE OF THE PLANT BASED ON THE DETERMINED GROWTH STATE.

S803 — ADJUST A LATERAL OFFSET OF A SPRAY PATTERN OF A NOZZLE BASED ON THE SIZE OR RADIUS TO TARGET ALIGNMENT OR MAXIMIZATION OF OVERLAP AREA OF A STRIP OF THE SPRAY PATTERN WITH THE CORRESPONDING ROOT ZONE.

S804 — COLLECT STEREO IMAGE DATA ON THE PLANT TO EVALUATE A PLANT SIZE OR HEIGHT TO VERIFY THE DETERMINED GROWTH STATE OR MATURITY STATE FOR THE PLANT.

S805 — ADJUST THE GROWTH STATE OR MATURITY STATE FOR THE PLANT BASED ON THE COLLECTED STEREO IMAGE DATA PREDOMINATING OVER REQUISITE GROWING DEGREE DAYS ESTIMATED BASED ON THE PLANTING DATE, THE CURRENT DATE, AND THE CROP TYPE.

FIG. 9

S801
DETERMINE A GROWTH STATE OR MATURITY STATE OF A PLANT BASED ON A PLANTING DATE, A CURRENT DATE AND THE CROP TYPE OF THE PLANT.

S802
ESTIMATE A SIZE OR RADIUS OF THE ROOT ZONE OF THE PLANT BASED ON THE DETERMINED GROWTH STATE.

S803
ADJUST A LATERAL OFFSET OF A SPRAY PATTERN OF A NOZZLE BASED ON THE SIZE OR RADIUS TO TARGET ALIGNMENT OR MAXIMIZATION OF OVERLAP AREA OF A STRIP OF THE SPRAY PATTERN WITH THE CORRESPONDING ROOT ZONE.

S806
SELECTIVELY ACTIVATE ONE OR MORE DIRECTIONAL NOZZLES OF A SPRAYER TO ADJUST A LATERAL OFFSET OF A DIRECTIONAL SPRAY PATTERN OF THE ONE OR MORE NOZZLES BASED ON THE SIZE OR RADIUS TO TARGET ALIGNMENT OR MAXIMIZATION OF OVERLAP AREA OF A STRIP OF THE SPRAY PATTERN WITH THE CORRESPONDING ROOT ZONE.

FIG. 10

S800
DETECT A HEIGHT OF A SAMPLE PLANT OR PLANTS IN ONE OR MORE ROWS OF CROP.

S805
DETERMINE A GROWTH STATE OR MATURITY STATE OF A PLANT BASED ON THE PLANT HEIGHT.

S802
ESTIMATE A SIZE OR RADIUS OF THE ROOT ZONE OF THE PLANT BASED ON THE DETERMINED GROWTH STATE.

S803
ADJUST A LATERAL OFFSET OF A SPRAY PATTERN OF A NOZZLE BASED ON THE SIZE OR RADIUS TO TARGET ALIGNMENT OR MAXIMIZATION OF OVERLAP AREA OF A STRIP OF THE SPRAY PATTERN WITH THE CORRESPONDING ROOT ZONE.

FIG. 11

METHOD FOR TREATING PLANTS WITH RESPECT TO ESTIMATED ROOT ZONES

RELATED APPLICATION

This document (including the drawings) claims priority and the benefit of the filing date based on U.S. provisional application No. 62/579,823, filed Oct. 31, 2017 under 35 U.S.C. § 119 (e), where the provisional application is hereby incorporated by reference herein.

FIELD

This disclosure relates to a method for treating plants with respect to estimated root zones.

BACKGROUND

Certain prior art sprayers may use a Y-drop sprayer configuration where two nozzles are arranged in an inverted Y to spray plants simultaneously in two adjacent rows. If the nozzles are fixed in position, the nozzles may not provide the sprayed liquid to target root zone or target foliage zone, where such zones can vary for application of nutrients versus other crop treatments, such as pesticide, herbicide, or fungicide. Accordingly, there is need for a system and method for spraying plants with automated nozzle selection.

SUMMARY

In accordance with one embodiment, a method for treating plants comprises determining a growth state or maturity state of a plant based on a planting date, a current date and the crop type of the plant. A root zone estimator or data processor estimating a size, diameter or radius of a root zone of the plant based on the determined growth state or maturity state. The data processor adjusts a lateral offset of a distribution pattern of a crop input or nutrient from at least one nutrient knife based on the size, diameter or radius of the root zone and safety zone about the root zone, where the at least one nutrient knife tracks a path outside (e.g., a substantially linear or arced path) of or bounded by the root zone.

BRIEF DESCRIPTION OF THE DRAWINGS

FIG. 8 is a flow chart of one embodiment of a method for treating or applying nutrients to plants.

FIG. 9 is a flow chart of another embodiment of a method for treating or applying nutrients to plants.

FIG. 10 is a flow chart of yet another embodiment of a method for treating or applying nutrients to plants.

FIG. 11 is a flow chart of still another embodiment of a method for treating or applying nutrients to plants.

DETAILED DESCRIPTION

As used in this document, "adapted to" means programmed with software instructions, arranged to, or configured to perform a task, calculation, estimation, communication, or other function set forth in the document with a logic device, data processor or other electronic structure.

Figure 1:
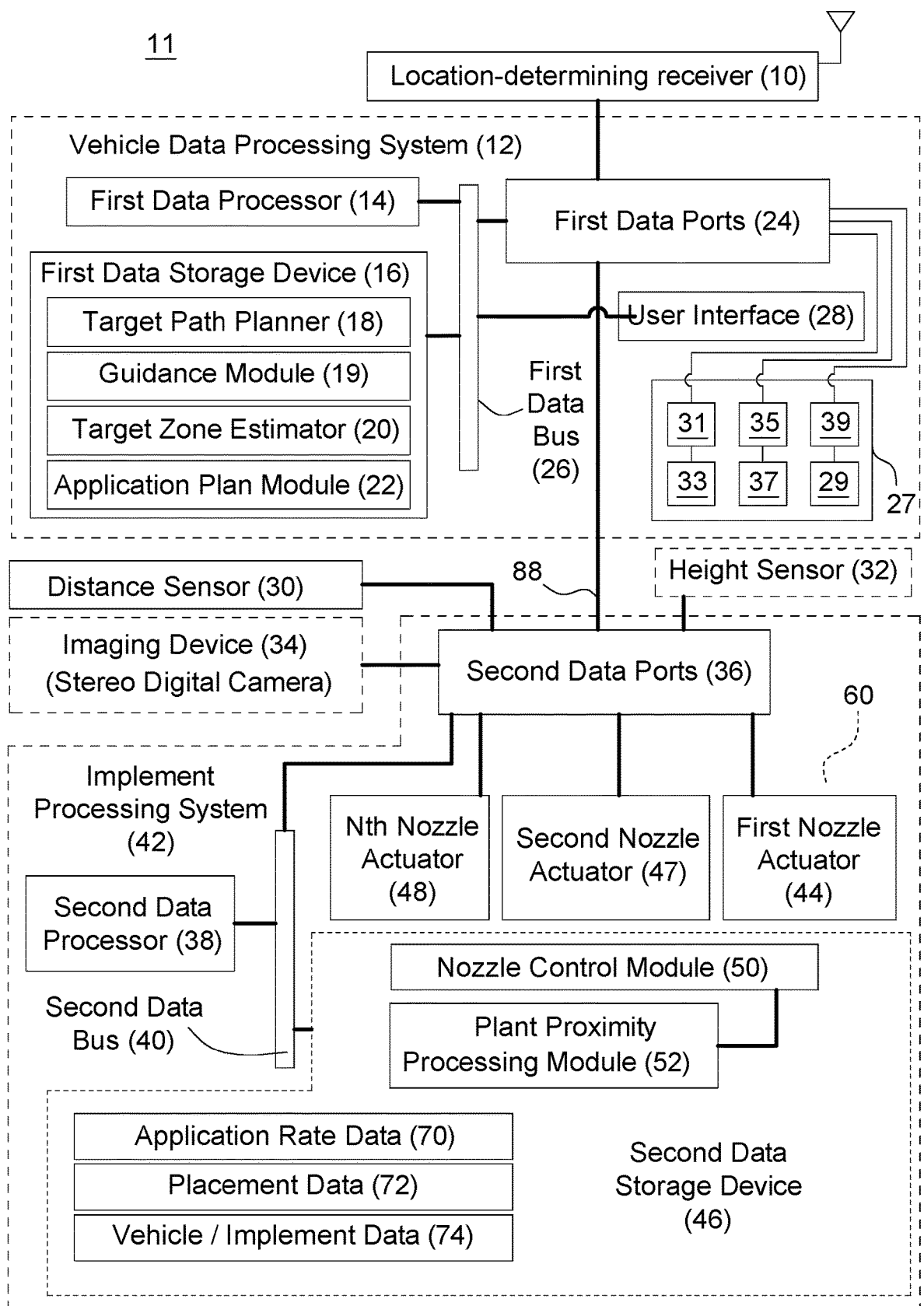
FIG. 1 is a block diagram of one embodiment of a system for spraying plants.

FIG. 1 is a block diagram of one embodiment of a system 11 for spraying plants. In one embodiment, the system 11 for spraying plants comprises a vehicle data processing system 12 and an implement data processing system 42. The vehicle data processing system 12 of FIG. 1 comprises a first data processor 14, a first data storage device 16, first data ports 24 and a user interface 28 coupled to a first data bus 26. The first data processor 14, the first data storage device 16, the data ports 24, and the user interface 28 can communicate with each other via the first data bus 26.

In one embodiment, a location-determining receiver 10 is coupled to at least one of the first data ports 24. A vehicle control system 27 is coupled to the first data ports 24 or the first data bus 26. For example, a steering controller 31, braking controller 35, and propulsion controller 39 may be coupled, directly to the first data ports 24, or indirectly to the vehicle data processing system 12 (or to the data ports) via a vehicle data bus 26. In turn, the steering controller 31 is connected to the steering system 33; the braking controller 35 is connected to the braking system 37; the propulsion controller 39 is connected to the propulsion system 29.

In one embodiment, the implement data processing system 42 comprises a second data processor 38, a second data storage device 46, and second data ports 36 coupled to a second data bus 40. The second data processor 38, the second data storage device 46, and the second data ports 36 can communicate with each other via the second data bus 40. In one embodiment, a distance sensor 30 (e.g., range sensor) and an optional crop height sensor 32 are coupled to the second data ports 36. In another embodiment, an optional imaging device 34 (e.g., stereo digital camera) is coupled to the second data ports 36. The optional crop height sensor 32 and the optional imaging device 34 are shown in dashed lines to indicate one or both are optional and may be deleted from certain configurations. In some configurations, the first data ports 24 and the second data ports 36 can communicate with each other via a communications line 88 or shared memory, for example.

The first data processor 14, the second data processor 38 or both comprise a microcontroller, a microprocessor, a digital signal processor, a programmable logic array, a logic device, an arithmetic logic unit, an application specific integrated circuit or another electronic processing device for inputting, outputting, processing or manipulating data.

The first data storage device 16, the second data storage device 46, or both comprises electronic memory, non-volatile random-access memory, an optical disc, an optical storage device, a magnetic disc, a magnetic storage device, a hard drive or another mechanism for storing, accessing and retrieving data.

In one embodiment, first data storage device 16 stores a target path planner 18 and guidance module 19, a target zone estimator 20 and an application plan module 22. Each module may comprise software, electronic hardware, or both.

The target path planner 18 provides a path plan for the vehicle 61 or sprayer to following in a field, such as a plan to make passes or swaths in the field to cover an enter field area with minimum overlap of crop inputs or sprayed materials 101. For example, the target path planner 18 may establish a path plan for the vehicle 61 to follow with a location-determining receiver 10 and a vehicle guidance module 19. The vehicle guidance module 19 can send command data or command signals to the steering controller 31, the braking controller 35, and the propulsion controller 39 via one or more data ports 24 or via the vehicle data bus such that the vehicle 61 tracks a path plan.

In one embodiment, a steering controller 31, a braking controller 35 and propulsion controller 39 communicate to the first data ports 24 via communication lines or a vehicle data bus, such as controller area network (CAN) data bus. In turn, the steering controller 31 communicates with the steering system 33, such as an electrohydraulic steering system 33 or an electrical steering system 33. The vehicle guidance module 19 generates command data or command signals to send steering commands to the steering controller 31 to track the path plan, target heading or target yaw, such as a target path where one or more nozzle assemblies are substantially centered between adjacent plant rows or plant row segments. The vehicle guidance module 19 may use position data form the location-determining receiver 10 or the optional imaging device 34, or both.

The braking controller 35 is coupled to a braking system 37, such as an electrohydraulic braking system 37, an electrical braking system 37 or a mechanical braking system 37. The braking controller 35 is coupled to a first data port.

The propulsion controller 39 is coupled to a propulsion unit, such as one more electric drive motors, an internal combustion engine, or an internal combustion engine that provides rotational mechanical energy to a generator or an alternator that provides electrical energy to one or more electric drive motors. The propulsion controller 39 is coupled to a first data port 24.

In one embodiment, a target zone estimator 20 estimates a target zone for applying crop inputs or treatments for application to plants, plant rows, plant row segments, soil zones, or soil. For example, crop inputs comprise insecticides, herbicides, fungicides, pesticides, chemicals, nutrients, nitrogen, phosphorus, potash, chemicals, or aqueous solutions for applying to treat plants or the soil. Each target zone may be associated with a corresponding waypoint, a range of waypoints, a path segment, a point or geographic location, such as a plant or plant row segment, along the path plan of the sprayer or vehicle 61. In one embodiment, the target zone estimator 20 determines or implements the zones, concentration, and amount of crop inputs applied for each corresponding waypoint, point or geographic location along the path plan of the sprayer or vehicle 61, which in turn may determine the number of nozzles of a nozzle assembly 60 that are activated on the boom and the positions or sections of nozzles that are activated on the boom by nozzle actuators (44, 47, 48).

In one configuration, the target zone estimator 20 can select from one of several strips (e.g., by activating a particular nozzle in a vertical array of nozzles or a nozzle assembly 60) that are parallel to each plant row (e.g., a geometric centerline of each plant row or center point) to direct or apply the crop inputs toward a selected one of the several strips, for a corresponding segment of each plant row. As used in this document, a nozzle assembly 60 shall be synonymous with a nozzle head. In one embodiment, the nozzle assembly 60 can provides a target first zone, second zone and third zone based on whether the row unit is centered between adjacent plant row segments and the lateral row spacing (or row width) between adjacent plant row segments. In a first example, even if the lateral row spacing or row width varies or if the nozzle assembly is laterally offset from a center point between the adjacent rows, the nozzle assembly 60 can compensate by activating, separately or collectively, different nozzles in each vertical array to target different zones on each side or opposite sides of the nozzle assembly 60. In a second example, the target zone estimator 20 or the nozzle control module 50 activates nozzles of the nozzle assembly 60 directed toward the first zone for a corresponding narrow width row, a second zone for a corresponding medium width row, and a third zone for a corresponding wide width row, where the narrow width row has less distance between adjacent row segments than the medium width row or the wide width row.

In one embodiment, the application plan module 22 estimates the crop inputs that are applied for a certain field along with a lateral distance or offset between a nozzle assembly 60 or nozzle and one or more plant rows. The PPP module 52 may estimate the lateral position of the sprayer or wheels based on the position data from the location-determining receiver 10 or distance data from one or more distance sensors 30 associated with the row unit to provide a distance estimate between the plant row (e.g., plant row segment) and the row unit or nozzle assembly 60. In one embodiment, the nozzle control module 50 can decide which nozzle in a vertical array of nozzles to activate for a row unit for any given waypoint, plant or section of plants in a row. Each nozzle assembly 60 and its actuators (or any optional data processor or controller) can communicate with the second data processor 38 via cable 204 (e.g., wiring or communications line and power line) and one or more second data portions 36.

In conjunction with the distance sensor 30, the location-determining receiver 10, the imaging device 34, and the plant proximity processing (PPP) module 52 may estimate the distance between one or more nozzles (of the nozzle assembly 60) and a corresponding row or rows of plants. The PPP module 52 may comprise a lateral position estimator that can estimate whether a lateral position of the sprayer or its wheels, or tracks or centered in a plant row or offset with respect to the center of the plant row to provide more concentrated application of crop input to certain area of foliage or a strip of ground relative to the row of plants.

In one embodiment, the distance sensor 30 may comprise an ultrasonic range finder, a laser range detector, an optical sensor that sends an ultrasonic signal, laser signal or optical signal, respectively, toward a plant row, a plant, a stalk, stem or trunk, a leaf canopy, or foliage to estimate or measure a lateral distance between a reference point on the boom or sprayer to the plant row, plant, leaf canopy, or foliage. For example, a laser range finder may comprise a light detection and ranging (LIDAR) device. In one embodiment, the reference point may be aligned with a reference nozzle, a nozzle assembly 60 or a central point, such as central vertical axis of supply lines 64 to a nozzle assembly 60 (e.g., Y-drop nozzle assembly). In an alternate embodiment, the distance sensor 30 may comprise a stereo imaging device.

In one embodiment, one or more rows of the sprayer vehicle 61 are associated with one or more corresponding distance sensors (30, 130R, 130L); the second data processor 38 may process or average distance estimates or measurements for a sampling interval to attain a median, mean, or mode distance (between the nozzle assembly 60 and the plant row unit) in the aggregate for all of the rows and associated row units (e.g., nozzle assemblies 60) of the vehicle 61. In other embodiments, one or more rows of the sprayer vehicle 61 are associated with corresponding distance sensors (130L, 130R in FIG. 4). For instance, a pair of distance sensors (130L, 130R) on the row unit or nozzle assembly 60 face opposite directions from each other; each distance sensor (e.g., 30, 130L or 130R) is configured to measure a distance between the row unit and a proximate plant portion of a corresponding plant row segment that each distance sensor faces.

Figure 4:
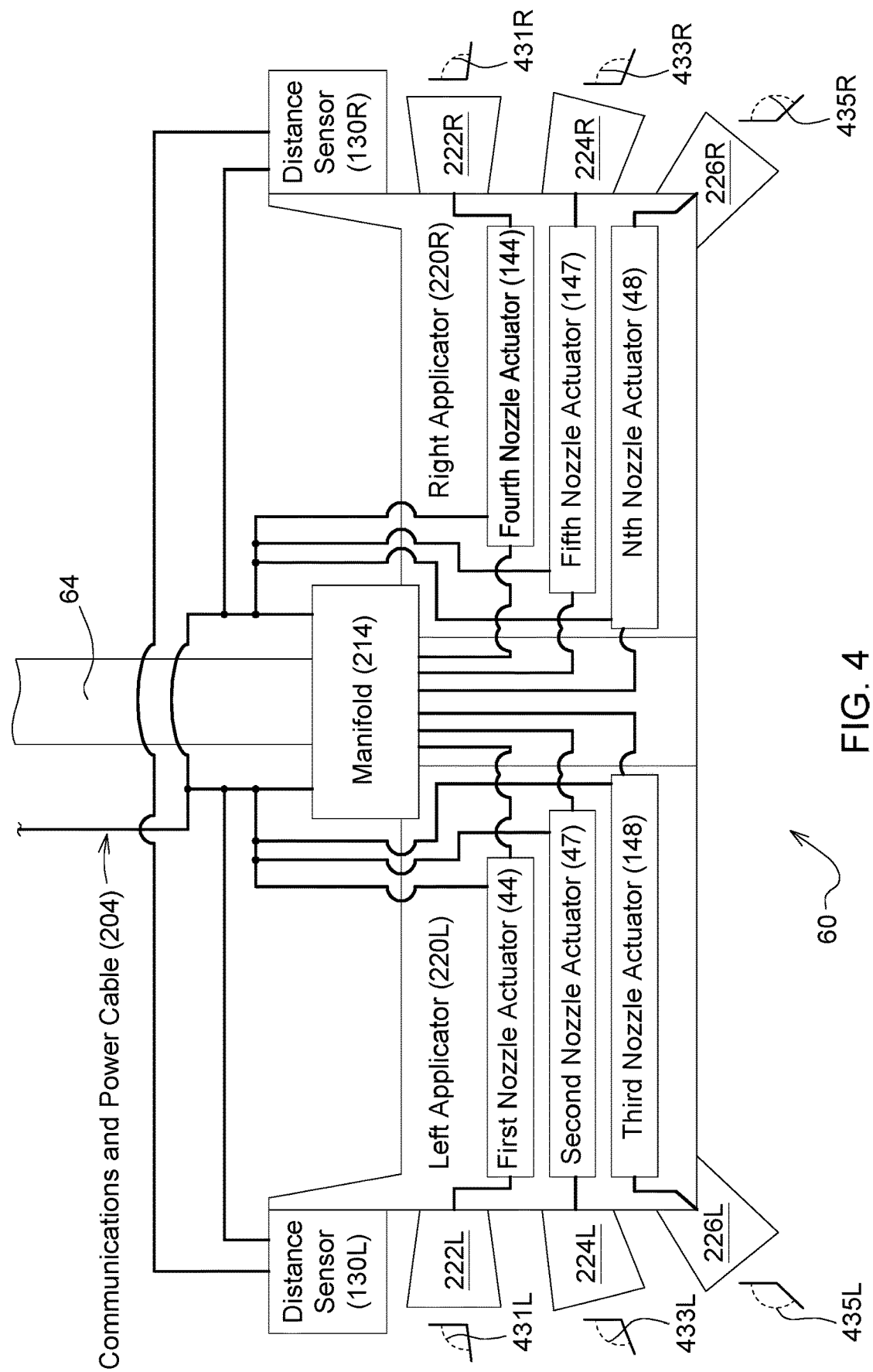
FIG. 4 is an enlarged view of the rectangular region 4 in FIG. 3, where the region includes a nozzle head.
Figure 5:
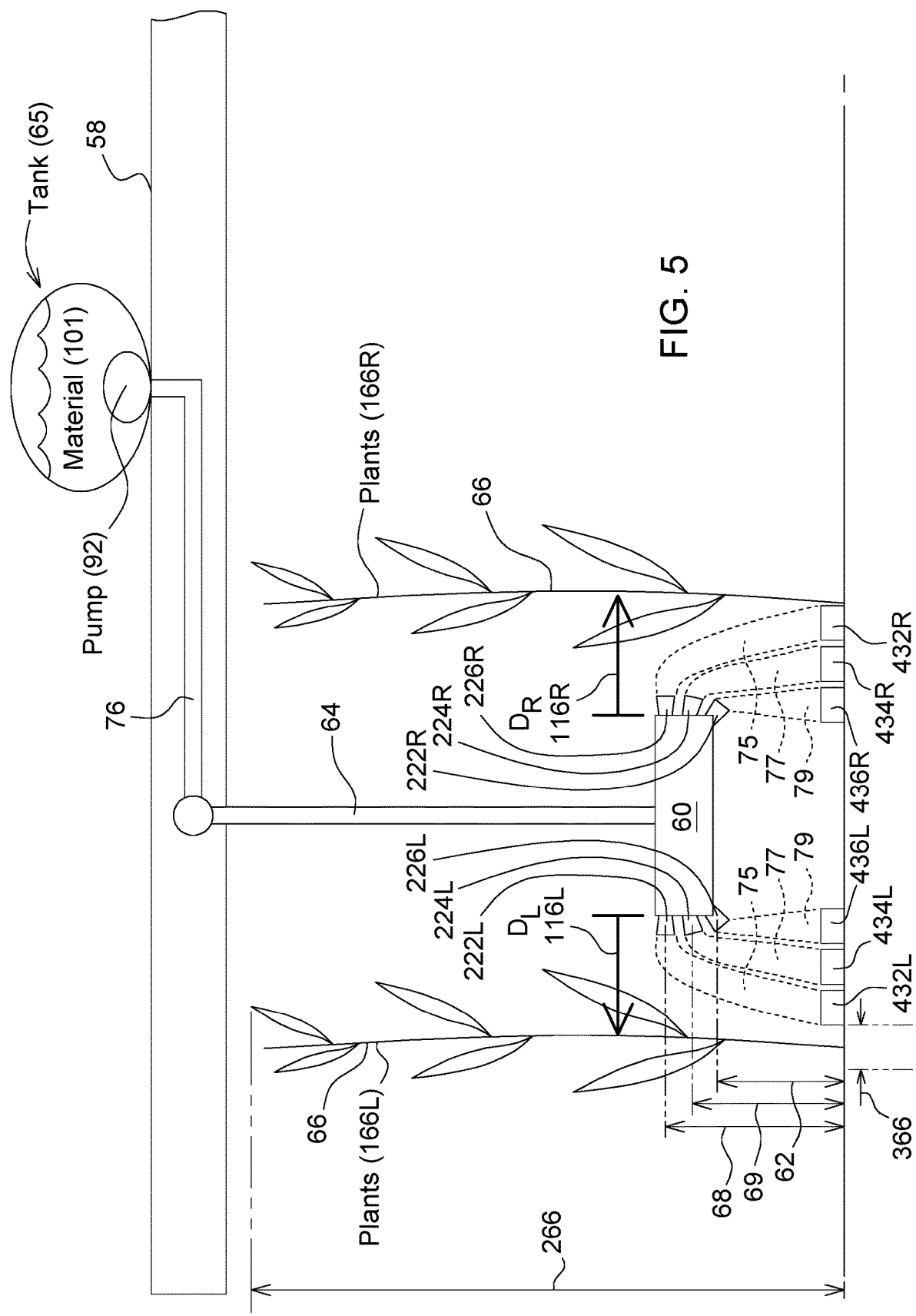
FIG. 5 illustrates a lateral separation or alignment of the nozzle head to adjacent rows of plants and target zones (e.g., target root zones) on the ground.

In one embodiment, as illustrated in FIG. 4 and FIG. 5, a set (e.g., pair) of first nozzles (222L, 222R) is associated with the row unit, where the first nozzles have corresponding first outlets facing different or opposite directions. Each of the first nozzles (222L, 222R) is directed toward a first zone (432L or 432R) with respect to the proximate plant portion of a corresponding plant row segment based on a first spray pattern 75 of each first nozzle (222L, 222R), where the set of first nozzles positioned above the second pair of nozzles in respective vertical arrays. A set (e.g., pair) of second nozzles (224L, 224R) is associated with the row unit or nozzle assembly 60, where the second nozzles (224L, 224R) have corresponding second outlets facing different or opposite directions. Each of the second nozzles (224L, 224R) is directed toward a second zone (434L or 434R) with respect to the proximate plant portion of a corresponding plant row segment based on a second spray pattern 77 of the second nozzle (224L, 224R). A set (e.g., pair) of third nozzles (226L, 226R) is associated with the row unit or nozzle assembly 60, where the third nozzles (226L, 226R) have corresponding third outlets facing different or opposite directions. Each of the third nozzles (226L, 226R) is directed toward a third zone (436L or 436R) with respect to the proximate plant portion of a corresponding plant row segment based on a third spray pattern 79 of the second nozzle.

Each nozzle assembly 60 for each row unit is controlled independently based on the corresponding distance measurement for its row that is measured by the distance sensor (30, 130L or 130R). A nozzle control module 50 selects or activates any two of the nozzles (222L, 224L, 226L, 222R, 224R, or 226R) of the nozzle assembly 60 based on maximum coverage of a target zone around the proximate plant portion of the one or more rows based on the first zone (432L, 432R), the second zone (434L, 434R), the third zone (436L, 436R) and the measured distance or measured distances that are measured by the distance sensor (30, 130L or 130R).

In one embodiment, an operator or user enters, via the user interface 28, an average, median or mode measurement of crop height samples taken in a field or portion of the field. The user interface 28 comprises one or more of the following: a display, a touch screen display, a keyboard, a keypad, and a pointing device (e.g., electronic mouse, touch pad or trackball).

In one embodiment, the optional height sensor 32 comprises an acoustic plant height sensor, an optical plant height sensor, a light detection and range (LIDAR) device, or a stereo vision imaging device. For example, an optical plant height sensor 32 may transmit particular frequency ranges of visible light, near infrared light and/or ultraviolet light at a plant row or plant from a fixed height on the sprayer or boom to generate a reflectance signal from the plant row or plant that is indicative of or proportional to the height of the plant row. Therefore, the plant height 266 can give some indication of the maturity of the plant or plant row and the corresponding root zone for a particular crop.

In one embodiment, the second data processor 38 or nozzle control module 50 commands or instructs the nozzle assembly 60, via actuators (44, 47, 144, 147), to activate said one or more nozzles (e.g., 222L, 222R) directed toward a first zone (432L, 432R) or to activate one or more nozzles (e.g., 224L, 222R) directed toward a second zone (434L, 434R) for plants that are greater than or at a threshold maturity level, where the first zone (432L, 432R) intercepts a plant base or plant stem 566 of a plant and wherein the second zone (222L) intercepts the root zone. In one example, threshold maturity level is greater than a V5 maturity level for maize or corn, such as a V5 to VT maturity level.

In one embodiment, the second data processor 38 or the nozzle control module 50 commands or instructs the nozzle assembly 60, via actuators (44, 47, 144, 147), to activate said one or more nozzles (e.g., 226L, 226R) directed toward a third zone (436L, 436R) spaced apart from the second zone (434L, 434R) by a lateral gap or safety gap to avoid over-applying or overdosing one or more plants with fertilizer, such as plants that are equal to or less than threshold maturity level. In one example, the threshold maturity level is less than V5 maturity level, such as a V5 to VE maturity for maize or corn plants. For example, maize or corn plants at the VE to V5 growth stage of maturity may be more susceptible to fertilizer damage than plants at the V6 to VT growth stage; hence, the target zone for VE to V5 growth stage may be further from the plant 66 (e.g., plant stem) then the target zone for V6 to VT growth stage.

In one embodiment, the plant proximity processing module 52 estimates the distance, such as the average, mean or mode distance between one or more plant rows to nozzle assembly 60, reference nozzle or reference point for each sampling interval. Further, the plant proximity processing module 52 may store a look-up table, database or other data structure that defines the relationship between a lateral offset of the sprayer, the sprayer nozzle, or nozzle assembly 60 and corresponding plant heights for a particular crop. In one configuration, the proximity processing module 52 or the data structure takes into consideration that the root zone of the plant or particular crop of a particular height may be associated with: (1) a lateral offset of the nozzle assembly 60 with respect to center point between adjacent plant rows, and/or (2) a vertical activation of one or more nozzles (222L, 224L, 226L or 222R, 224R or 226R) in vertical array of nozzles at different corresponding heights (68, 69, 62) above ground level, and different respective target zones with respect to plant row segments.

In one embodiment, nozzle control module 50 (e.g., nozzle selection module) determines whether to activate a first nozzle actuator 44, a second nozzle actuator 47, a third nozzle actuator 148, fourth nozzle actuator 144, a fifth nozzle actuator 147, and/or an Nth actuator 48, where N equals any positive integer or whole number greater than 2. The target zone estimator 20, the application plan module 22, and the plant proximity module 52, the first data processor 14, and the second data processor 38 may provide input to the nozzle control module 50 for selection of appropriate number, location, radiation pattern, pressure, or other parameters of activated or deactivated nozzles. The nozzle control module 50 may communicate with one or more actuators (44, 47, 148, 144, 147, 48) via the second data ports 36. However, in an alternate embodiment, the nozzle control module 50 may comprise an electronic controller (e.g. that is housed in the nozzle assembly 60 or separately from the second data storage device 46) and that is located between one or more second data ports 36 and the nozzle actuators (44, 47, 148, 144, 147, 48).

In one configuration, an optional imaging device 34 comprises a stereo vision imaging device or digital stereo vision camera with image data processing. The stereo images of the plants or plant rows can provide guidance information that used separately or cumulatively with location data or motion data from the location-determining receiver 10 to guide the vehicle 61 or sprayer relative to the plant rows, such as the lateral position (e.g., centered between adjacent rows of plants or offset) of the sprayer, implement, nozzle assembly 60 or nozzle within the plant rows. Further, the second data processor 38, alone or in combination with the second data storage device 46, comprises an imaging processing module 91 for applying image processing to the collected image data, such as color differentiation to distinguish background pixels from plant pixels. Background pixels may represent the ground, clouds, the sky or other background pixels, whereas the plant pixels may have some shade of green, flowers, fruit, seed pods, ears, or other plant foliage color consistent with a reference database or range of plant pixels for a particular crop type. The image processing module 91 may be adapted (e.g., programmed with software instructions) determine a cloud or constellation of data points of the plant pixels that represent plant height of the plant rows or plants.

In accordance with one embodiment, a method or system for spraying plants comprises a location-determining receiver 10 for estimating a position of a sprayer or vehicle 61 with respect to one or more rows of plants based on collected plant location data from a location-determining receiver 10, an imaging device 34, or other data source.

The collected plant location data can indicate a position of a respective row of plants. The collected plant location data can be estimated in accordance with various techniques, which may be applied separately or cumulatively. Under a first technique, during planting or seeding of the plant rows, a location-determining receiver (e.g., 10) on the planter, tractor or implement, provides an as-planted map of the plant rows or plant locations in one or more fields. For instance, the as-planted map may be stored in or transferred to (e.g., wirelessly transferred to) the first data storage device 16, the second data storage device 46 or in a data storage medium.

Under a second technique, the plant locations or plant locations can be defined by a series of points (e.g. geographic coordinates) that define substantially linear segments, curved segments, contours or spirals. Under a third technique, a planting plan for the planter provides a map of plant rows or plant locations in one or more fields that can be used by the location-determining receiver 10 and guidance system of the planter to plant the seeds or plants. Under a fourth technique, plant rows or plant locations can be defined by linear or quadratic equations that are bounded by field boundaries.

If a distance sensor (30, 130L or 130R) is not used or is not available, an optional imaging device 34 (in FIG. 6) can be arranged to measure a distance between a nozzle assembly 60 (e.g., nozzle head) and a plant 66 (e.g., plant stem) or a series of plants 66 (e.g., plant stems). A guidance module 19 is adapted to align the vehicle 61; hence, the nozzle assembly 60 with a target path between the rows of plants, such as a centered path between the rows, or a lateral offset between the rows of the plants. A first nozzle (222L or 222R) is targeted toward a first zone (432L or 432R, respectively) with a first lateral spacing with respect to the plant 66 (e.g., plant stem) or plant row segment based on a first spray pattern 75 of the first nozzle (222L or 222R).

A second nozzle (224L or 224R) is targeted toward a second zone (434L or 434R, respectively) with a second lateral spacing with respect to the plant 66 (e.g., plant stem) or plant row segment based on a second spray pattern 77 of the second nozzle. Further, a third nozzle (226L, 226R) is targeted toward a third zone (436L, 436R, respectively) with a third lateral spacing with respect to the plant 66 (e.g., plant stem) based on the third spray pattern 79 of the third nozzle (226L, 226R).

In one configuration, the first nozzle (222L, 222R) may have a greater height 68 above ground than a height 69 of the second nozzle (224L, 224R). The first nozzle (222L, 222R) and the second nozzle (224L, 224R) may be arranged in a substantially vertical array, such as a left vertical array (or left applicator 220L) on a left side of the nozzle assembly 60 or a right vertical array (or right applicator 220R) on a right side of the nozzle assembly 60.

In another configuration, each nozzle assembly 60 has a left vertical array of nozzles (e.g., first nozzle 222L, second nozzle 224L and third nozzle 226L) and a right vertical array of nozzles (e.g., first nozzle 222R, second nozzle 224R and third nozzle 226R). A first nozzle set comprises a pair of upper nozzles or first nozzles (222L, 222R) on the row unit or nozzle assembly 60 facing opposite directions toward a left first zone 432L and a right first zone 432R associated with adjacent rows of plants. A second nozzle set comprises a pair of intermediate nozzles or second nozzles (224L, 224R) on the row unit or nozzle assembly 60 facing opposite directions toward a left second zone 434L and a right second zone 434R. Further, a third nozzle set comprises a pair of lower nozzles or third nozzles (226L, 226R) on the row unit or nozzle assembly 60 facing opposite directions toward a left third zone 436L and right third zone 436R.

In one embodiment, the first nozzle (222L, 222R) comprises an upper nozzle at an upper height 68 above the ground and wherein the second nozzle (224L, 224R) comprises an intermediate nozzle at an intermediate height 69, respectively) above the ground. In an illustrative example, the upper nozzle or first nozzle (222L, 222R) is directed at a first down-tilt angle 431 with respect to the vertical axis toward the first zone (432L, 432R) the intermediate nozzle or second nozzle (224L, 224R) is directed at a second down-tilt angle 433 with respect to a vertical axis toward the second zone (434L, 434R). In one embodiment, a lower nozzle or third nozzle (226L, 226R) is at a lower height above ground below the intermediate nozzle, wherein the lower nozzle is directed at a third down-tilt angle 435 with respect to a vertical axis toward a third zone (436L, 436R).

A nozzle control module 50 is adapted to control, select, or activate automatically one or more of the nozzles of the nozzle assembly 60 based to cover the first zone (432L, 432R), the second zone (434L, 434R), or both as a target zone for the plant row segment based on the measured distance. For example, the nozzle control module 50 is adapted to control, select or activate any permutation or combination of a first nozzle (222L, 222R), a second nozzle (224L, 224R) and/or a third nozzle (226L, 226R) based on maximum coverage (with a sprayed crop input) of a target zone around the plant 66 (e.g., plant stem), a plant row, or a series of plants 66 (e.g., stems) based on the first zone (432L, 432R), the second zone (434L, 434R), the third zone (436R, 436L) and the measured distance (116L, 116R). In some configurations, the first zone (432L, 432R), second zone (434L, 434R) and third zone are configured as strips that are parallel to each other and with respect to one or more plant rows, where the first zone (432L, 432R), second zone (434L, 434R) and third zone (436R, 436L) are associated with a corresponding plant row.

In another embodiment, the nozzle control module 50 (e.g. nozzle selection module) controls or selects the nozzle assembly 60. The nozzle control module 50 may comprise an electronic controller. In particular, the nozzle control module 50, the plant proximity module 52, or both may comprise electronic devices that are separate from the second data storage device 46 and that are not stored in the second data storage device 46. For example, the nozzle control module 50 controls or selects the nozzle based on one or more measured distances (116L, 116R) and user input of the crop input, such as whether the crop input comprises a nutrient or a non-nutrient application, where the target zone for nutrient crop inputs is directed toward a ground zone with reference to the plant 66 (e.g., plant stem) and wherein the target zone for non-nutrient crop inputs is directed toward a foliage zone with respect to the plant 66 (e.g., plant stem) or plant foliage.

In one embodiment, an optional plant height sensor 32 or imaging device 34 may estimate the height of the plant or segment of a row of plants, which can be assigned one or more target zones or foliar target zones. Alternately, the user may enter, via the user interface 28, the average or mean plant height in a field or from a prior survey of a field by an unmanned aerial vehicle.

In another embodiment, the nozzle control module 50 selects one or more active nozzles on the nozzle assembly 60 based on at least one of the measured distance (116L, 116R), an observed height (68, 69, 62) of the nozzle with respect to ground and any offset between the nozzle assembly 60 with respect to a target path between the rows of plants. Alternately, the user may input the observed height (68, 69, 62) of the nozzle with respect to the ground or input a sprayer vehicle 61 make and model number that is associated with such observed height information (68, 69, 62).

In another embodiment, the nozzle control module 50 (e.g., nozzle selection module) selects one or more nozzles on the nozzle assembly 60 based on at least one of the measured distance (116R, 116L), an observed location of the sprayer in the field, and any offset between the nozzle head with respect to a target path between the rows of plants. In one example, the nozzle control module 50 can reduce the lateral width of the spray pattern on demand for a particular crop row segments with normal than targeted row width (between two adjacent crop rows) to provide uniform application of fertilizer to crop rows or to apply fertilizer in accordance with differential application requirements. Similarly, in another example, as the sprayer vehicle 61 makes turns or headland turns, as sensed by a change in the heading or yaw rate of the vehicle 61 from the location-determining receiver 10, inertial measurement unit of the location-determining receiver 10, or accelerometer (e.g., of the location-determining receiver 10), the second data processor 38 or the nozzle control module 50 can reduce dynamically the lateral width of the spray pattern on demand to avoid overspray or unwanted application of fertilizer, unwanted application of herbicide, or crop inputs that might damage crops or other vegetation. A change in the heading, a mathematical derivative of the heading, or yaw rate or accelerometer data can be indicative of a turn of the sprayer vehicle 61, for instance.

In one embodiment, a target path comprises a centered path between adjacent ones of the rows where distances measured by the pair of distance sensors 30 are approximately equal and where the nozzle control module 50 selects or activates (simultaneously) via one or more actuators the pair of first nozzles (e.g., right upper nozzle 222L and left upper nozzle 222R) or the pair of the second nozzles (e.g., right lower nozzle 226L or right intermediate nozzle 224L, and left lower nozzle 226R or left intermediate nozzle 224R). The target path comprises an offset path between adjacent ones of the rows where distances measured by the pair of distance sensors (30, 130L, 130R) are different by at least a minimum threshold and wherein the nozzle selection module selects or activates one of the first nozzles (222L, 222R) and one the second nozzles (224L, 224R) such that the different zones (e.g., strips on the soil or on the plant row segments) are substantially targeted for adjacent rows of the plants.

The nozzle control module 50 is adapted to select or activate nozzles on the row units or nozzle assemblies 60 independently from the other row units (or in synchronization or coordination with the other row units on the implement) based on the measured distances from the corresponding pair of distance sensors (30, 130L, 130R) and based on the location of the sprayer in the field. For example, the nozzle control module 50 is adapted to select or control the nozzles on the row unit such that there is compensation in the spray patterns for growth variation in the rows of plants or variation or error in the as-planted spacing between adjacent rows of plants. For example, the compensation in the spray patterns can account for guess rows or errors in adjacent passes or swaths of planters, for manually driven planting, or for planting without use of precise position data from a satellite navigation receiver 10.

As used in this document, the proximate plant portion comprises a closest or nearest plant stem (66 166L, 166R) in a row of crop. In one configuration, the first zone (432L, 432R) and second zone (434L, 434R) comprise adjacent bands or strips on the ground near the proximate plant portion. Further, a third zone (436L, 436R), which comprises a central zone closest to the center point or centerline, between adjacent plant row segments may be adjacent band or strip to the second zone. Although in some configurations there is no or minimal overlap between the first zone (432L, 432R) and the second zone (434L, 434R), or between the second zone and third zone (436L, 436R), in other configurations there may be overlap between any two zones.

In one configuration, the first data processor 14 and the user interface 28 facilitate proper control of the spray patterns (75, 77, 79) from each nozzle assembly 60. As noted, a first data processor 14 is capable of communication with the guidance module and a user interface 28 is coupled to the first data processor 14. Data may be inputted into the user interface 28 in accordance with various examples, which may be applied separately or cumulatively. In first example, the user interface 28 supports entry of the crop input and ancillary data including any of the following: (1) whether the crop input comprises a nutrient or a non-nutrient application, and (2) if the crop is for nutrient application, the growth stage, planting date 83 or height of the crops or plants. In second example, the user interface 28 supports entry of the average, median, or mean plant height in a row, field or zone of crop, or the average, median or mean lateral width or span of the leaf canopy of the plant in a row, field or zone of crop. In a third example, a user interface 28 is coupled to the first data processor 14, the user interface 28 supporting entry of observed height of the nozzle with respect to the ground or input a sprayer make and model number that is associated with such observed height information.

Based upon one or more of the examples of data inputted into the user interface 28, the first data processor 14 or the nozzle control module 50 may adjust the target zone for nutrient crop inputs to be directed toward a certain zone (e.g., first zone (432L, 432R), second zone (434L, 434R), third zone (436L, 436R) or ground zone) with a corresponding lateral separation distance 366 with reference to the plant 66 (e.g., plant stem). Similarly, the first data processor 14 may direct the target zone for non-nutrient crop inputs to be directed toward a foliage zone with respect to the plant stem (66, 166L, 166R) or plant foliage.

In one embodiment, a first distance sensor (30 or 130L) on a first side of the row unit estimates a first estimated distance between the row unit and a first plant or first row of plants. In addition, a second distance sensor (30 or 130R), on a second side of the row unit opposite the first side, estimates a second estimated distance between the row unit and second plant or second row of plants. Accordingly, nozzle control module 50 is adapted to select different ones of the nozzles, on opposite sides of the row unit if the first estimated distance differs from the second estimated distance.

In an alternate embodiment, a plant height sensor 32 or imaging device 34 is adapted to estimate a plant height 266 of the plants in plant rows, which can be assigned one or more corresponding target zones or foliar target zones. In turn, the second data processor 38 or the nozzle control module 50 selects or activates one or more nozzles (222L, 224L, 226L, 222R, 224R, 226R) via a corresponding actuators (44, 47, 148, 144, 147, 48, respectively) based on at least one of the measured distance, an observed height (62, 69, 68) of the nozzle with respect to ground, the observed position of the sprayer vehicle 61, and any lateral offset between the nozzle assembly 60 with respect to a target path (e.g., center point or center line, spaced equidistantly to each plant row stem) between the rows of plants.

Figure 2:
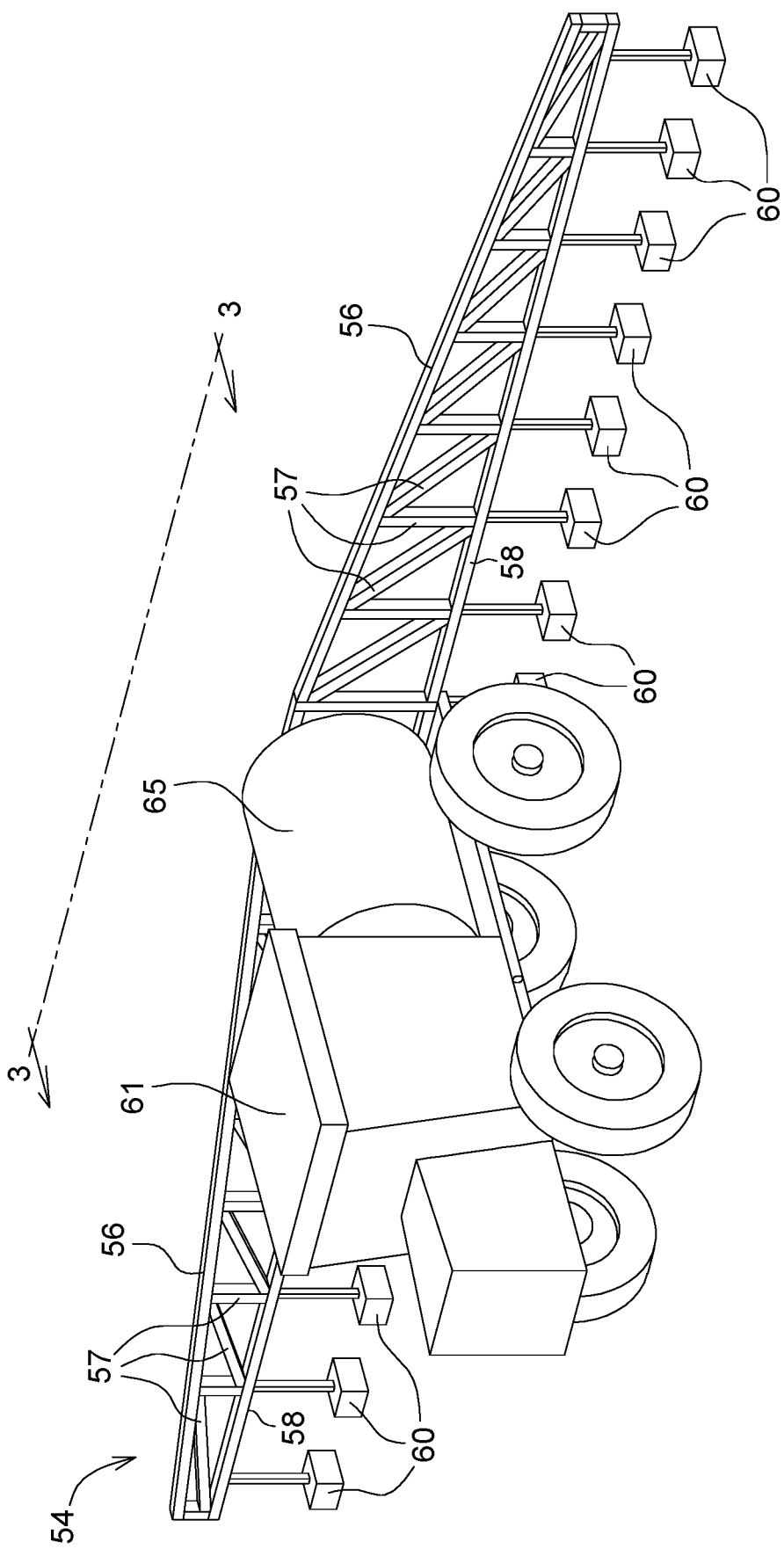
FIG. 2 is a perspective front view of an illustrative sprayer vehicle and implement that hosts the system of FIG. 1.

FIG. 2 is a perspective front view of an illustrative sprayer vehicle 61 and implement that hosts the system of FIG. 1. The sprayer vehicle 61 has a tank 65 or tows a trailer with a tank 65 thereon, where the tank 65 contains crop inputs for spraying or application to plants, soil, or the field. The sprayer vehicle 61 supports boom assembly 54. As illustrated in FIG. 2 and in FIG. 3, the boom assembly 54 comprises a lower boom member 58 and an upper boom member 56 that are connected via a boom braces 57. The boom assembly 54 supports one or more nozzle assemblies 60 or nozzle heads per row unit. For example, a primary nozzle assembly 60 is supported by the boom 54 to treat or spray a first row and a second row of crop, whereas a secondary nozzle assembly 60 is supported by the boom 54 to treat or spray a second row of crop and a third row of crop, where the nozzle control module 50 controls, separately and independently, or in synchronization or coordination, the primary nozzle assembly 60 and the second nozzle assembly 60 for the targeted application of crop inputs and coverage of the crop inputs. Each primary and second nozzle assembly 60 may contain one or more vertical arrays of nozzles. A first vertical array is defined by an array of left nozzles (222L, 224L, 226L), whereas a second vertical array of nozzles (222R, 224R, 226R) is defined by an array of second nozzles. The nozzle assemblies 60 are fed via supply lines (76, 64) that are connected or coupled to the tank 65 or a pump 92 associated with the tank 65 that contains material 101 or other crop input.

Figure 3:
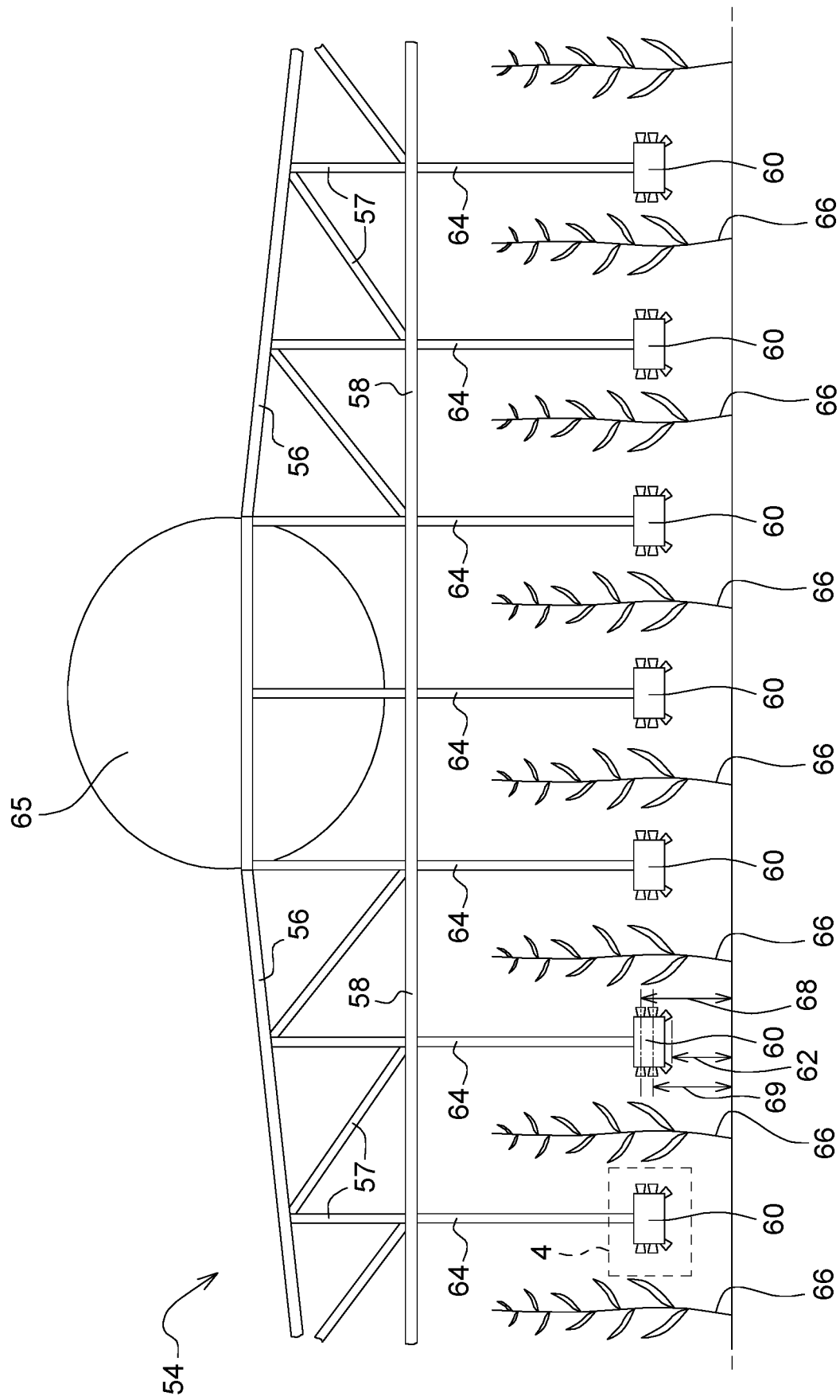
FIG. 3 is a rear view of the sprayer implement of FIG. 2 as viewed along reference line 2-2 of FIG. 2.

FIG. 3 is a rear view of the sprayer implement of FIG. 2 as viewed along reference line 2-2 of FIG. 2. FIG. 3 is similar to FIG. 2, except FIG. 2 shows the relation of respective nozzle assemblies 60 to corresponding plant rows (of plants or plants 66 (e.g., stems)) of the sprayer vehicle 61. Each nozzle assembly 60 has a vertical array of nozzles. As illustrated, each nozzle assembly 60 has a pair of lower nozzles (226L, 226R), a pair of intermediate nozzles (224L, 224R) and a pair of upper nozzles (222L, 222R). Each lower nozzle or pair of lower nozzles (226L, 226R) has a lower nozzle height 62. Each intermediate nozzle or pair of intermediate nozzles (224L, 224R) has an intermediate nozzle height 69. Each upper nozzle or pair of upper nozzles (226L, 226R) has an upper nozzle height 68.

FIG. 4 is an enlarged view of the rectangular region 4 in FIG. 3, where the region 4 includes a nozzle head or nozzle assembly 60. For each row unit, a vertical supply line 64 is connected to an input port of a manifold 214. Output ports of the manifold 214 are coupled to nozzles (222L, 224L, 226L, 222R, 224R, 226R) via nozzle actuators (44, 47, 148, 144, 147, 48), such as electrohydraulic valves, that control the flow (e.g., on or off, or volume and pressure) of fluid between the manifold 214 and the nozzles to produce a desired spray pattern or radiation pattern of one or more crop inputs. The nozzle actuators (44, 47, 148, 144, 147, 48) are associated with a communications and power lines that provide communications from the implement data processing system 42 and electrical energy to power the nozzle actuators (44, 47, 148, 144, 147, 48) and distance sensors (30, 130L, 130R) of each nozzle assembly 60. Fluid or liquid that contains, suspends or dissolves crop inputs are hydraulically communicated or conveyed from the tank 65 to the nozzles via the supply lines (64, 76) and manifold 214. As shown, the distance sensor comprises a right distance sensor (30 or 130R) and a left distance sensor (30 or 130L), where the left distance sensor 130L determines a left range or left distance between a left side of the nozzle assembly 60 and first plant row and wherein a right distance sensor (30 or 130R) determines a right range or right distance between a right side of the nozzle assembly 60 and a second plant row that is separated from the first plant row and adjacent to the first plant row. The second data processor 38 may use the right range or right distance and the left range or the left distance to estimate the lateral position of the row unit or nozzle assembly 60 between rows of plants; hence, adjust the control, selection or activation differentially of certain (pairs of) right and left nozzles to compensate for the lateral offset (of the nozzle assembly from a center point between adjacent rows of plants (166R, 166L)) and still deliver uniform spray pattern coverage (e.g., uniform dosing/application/concentration) of crop input to both rows of plants (e.g., with a spray pattern that uses different nozzles on the right and left sides of the nozzle assembly 60).

As illustrated in FIG. 4, the pair of upper nozzles comprises a left upper nozzle 222L and a right upper nozzle 222R, where the upper left nozzle 222L has a first down-tilt angle 431L and a right upper nozzle 222R has a first down-tilt angle 431R from a substantially vertical axis; the pair of intermediate nozzles comprises a left intermediate nozzle 224L and a right intermediate nozzle 224R, where the left intermediate nozzle 224L has a second down-tilt angle 433L and the right intermediate nozzle 433R has a second down-tilt angle 433R from a substantially vertical axis; the pair of lower nozzles comprises a left lower nozzle 226L and a right lower nozzle 226R, where the left lower nozzle 226L has a third down-tilt angle 435L from a substantially vertical axis and where the right lower nozzle 226R has a third down-tilt angle 435R from the vertical axis. In one embodiment, the first down-tilt angle is less than the second down-tilt angle. Further, the second down-tilt angle is less than the third down-tilt angle.

In one embodiment, the nozzle control module 50 is capable of selecting a new combination or permutation of nozzles of each nozzle assembly 60 for each time interval for substantial alignment with a dynamically adjustable target zone associated with corresponding plant row segments based on the observed position of the sprayer vehicle 61 in the field. As the sprayer vehicle 61 moves through the field, each nozzle assembly 60 or row unit faces a series of adjacent row segments with: (1) potentially different spacing or different lateral offset to the nozzle assembly 60 with respect to a center point or center line between adjacent plant row segments, (2) potentially different growth stages of plants or crop input requirements, (3) potentially different prescriptions for crop inputs based on zones. The second data processor 38 and the nozzle control module 50 can control, activate and deactivate nozzles of each nozzle assembly 60 on the boom 54 to provide the proper or appropriate customized application of crop inputs for each row segment, such as by directing, on a row-by-row basis, the spray pattern toward one or more left zones or rights zones on each side of the nozzle assembly 60. Within the left applicator 220L or vertical nozzle array of the nozzle assembly 60, a set of nozzle actuators (44, 47, 148) can selectively and independently actuate, control (e.g., volume and/or pressure) activate or deactivate any one or more nozzles, including any permutation of activated nozzles or deactivated nozzles or one or more corresponding intervals as the sprayer vehicle 61 moves or progresses through the field. Within the right applicator (220R) or vertical nozzle array of the nozzle assembly 60, a set of nozzle actuators can selectively and independently control actuate, activate or deactivate any one or more nozzles, including any permutation of activated nozzles or deactivated nozzles for an interval as the sprayer vehicle 61 progresses through a field with two or more rows.

The first nozzle actuator 44 can dynamically control, activate or deactivate the corresponding left upper nozzle 222L for one or more intervals in response to control signals or data from the nozzle control module 50 (or the second data processor 38) and position data from the location-determining receiver 10, consistent with: the target placement data 72, vehicle/implement data 64 and/or application rate data 70 for the applied or sprayed crop inputs. The second nozzle actuator 47 can control, activate or deactivate the corresponding left intermediate nozzle 224L for one or more intervals in response to control signals or data from the nozzle control module 50 (or the second data processor 38) and position data from the location-determining receiver 10, consistent with the target placement data 72, application rate data 70 and vehicle/implement data 64 for the applied or sprayed crop inputs. The third nozzle actuator 148 can control, activate or deactivate the corresponding left lower nozzle 226L for one or more intervals in response to control signals or data from the nozzle control module 50 (or the second data processor 38) and position data from the location-determining receiver 10, consistent with the target placement data 72, application rate data 70 and/or vehicle implement data 74 for the applied or sprayed crop inputs. The fourth nozzle actuator 144 can control, activate or deactivate the corresponding right upper nozzle 222R for one or more intervals in response to control signals or data from the nozzle control module 50 (or the second data processor 38) and position data from the location-determining receiver 10, consistent with the target placement data 72, application rate data 70, vehicle/implement data 74 for the applied or sprayed crop inputs. The fifth nozzle actuator 147 can control, activate or deactivate the corresponding right intermediate nozzle 224R for one or more intervals in response to control signals or data from the nozzle control module 50 (or the second data processor 38) and position data from the location-determining receiver 10, consistent with the target placement data 72, application rate data 70 and vehicle implement data 74 for the applied or sprayed crop inputs. The Nth nozzle actuator 48 (e.g., sixth nozzle actuator) can control, activate or deactivate the corresponding right lower nozzle 226R for one or more intervals in response to control signals or data from the nozzle control module 50 (or the second data processor 38) and position data from the location-determining receiver 10, consistent with the target placement data 72, application rate data 70, and vehicle/implement data 74 for the applied or sprayed crop inputs.

FIG. 5 illustrates a lateral separation or alignment of the nozzle assembly 60 to adjacent rows of plants (66, 166L, 166R) and target zones (e.g., target root zones) on the ground. The tank 65 in FIG. 5 contains fluid or liquid material 101, such as a crop input for spraying or application to crop, plants or the soil, or pests or weeds within the vicinity of the crop, plants or soil. The pump 92 in or external to the tank 65 is capable of pumping the fluid or liquid material 101 to the nozzle assembly 60 or nozzle head via a network of supply lines (76, 64).

A best illustrated in FIG. 5, the nozzles (222L, 224L, 226L, 222R, 224R, 226R) are directed toward different target zones or strips, which are associated with the ground near a left plant row and right plant row. However, in other configurations, it is understood that the nozzles (222L, 224L, 226L, 222R, 224R, 226R) can be configured to direct the target zones or strips at foliage above the ground. As shown in FIG. 5 the left nozzles (222L, 224L, 226L) are arranged in a vertical array comprising the left upper nozzle 222L at an upper height 68 above ground, a left intermediate nozzle 224L at an intermediate height 69 above ground, and a left lower nozzle 226L at a lower height 62 above ground. The left upper nozzle 222L has a first spray pattern 75 or an upper spray pattern directed at a left first zone 432L, which has the closest lateral offset 366 to the left plant row 166L. The left intermediate nozzle 224L has a second spray pattern 77 or an intermediate spray pattern directed at a left second zone 434L, which has an intermediate lateral offset to the left plant row 166L. The left lower nozzle 226L has a third spray pattern 79 or lower spray pattern directed at a third first zone 436L, which is closest to a central point between the two adjacent plant rows or which has the greatest lateral offset to the left plant row (e.g., a stem or trunk of one or more plants in the left plant row).

The implement data processing system 42 or the nozzle control module 50 selects or controls the appropriate or proper activation of one or more nozzles within the left array (222L, 224L, 226L) of the nozzle assembly 60 to cover any combination of one or more following zones: the left first zone 432L, the left second zone 434L or left intermediate zone, and the left third zone 436L, which may be based on an observed or measured distance between the left plant row and the nozzle assembly 60, or an observed or measured distance between the right plant row and the nozzle assembly 60, along with botany, plant science, agronomic data, agricultural prescriptions, or horticultural recommendations. For example, the crop input (e.g., fertilizer or soil treatment) may be targeted to a certain root zone of a treated plant or treated segment of the (left) crop row based on: the crop maturity level, crop height, the lateral width of the foliage, or lateral width leaf canopy of the crop row, as observed by sensors or input data entered by an operator of the sprayer vehicle 61.

As shown in FIG. 5 the right nozzles (222R, 224R, 226R) are arranged in a vertical array comprising the right upper nozzle 222R at an upper height 68 above ground, a right intermediate nozzle 224L at an intermediate height 69 above ground, and a right lower nozzle 226R at a lower height 62 above ground. The right upper nozzle 222R has a first spray pattern 75 or an upper spray pattern directed at a right first zone 432R, which has a closest lateral offset to the right plant row of plants 166R. The right intermediate nozzle 224R has a second spray pattern 77 or an intermediate spray pattern directed at a right second zone 434R, which has an intermediate lateral offset to the right plant row of plants 166R. The right lower nozzle 226R has a third spray pattern 79 or lower spray pattern directed at a third first zone 426R, which is closest to a central point between the two adjacent plant rows or which has the greatest lateral offset to the right plant row (e.g., a stem or trunk of one or more plants in the right plant row) of plants 166R. The implement data processing system 42 or the nozzle control module 50 selects or controls the appropriate or proper activation of one or more nozzles within the right array of the nozzle assembly 60 to cover any combination of one or more following zones: the right first zone 432R, the right second (or right intermediate) zone 434R and/or the right third zone 436R, which may be based on an observed or measured distance between the left plant row and the nozzle assembly 60, or an observed or measured distance between the right plant row and the nozzle assembly 60, along with botany, plant science, agronomic data, agricultural prescriptions or horticultural recommendations. For example, the crop input (e.g., fertilizer or soil treatment) may be targeted to a certain root zone of a treated plant 66 or treated segment of the (right) crop row based on: the crop maturity level, crop height or plant height 266, the lateral width of the foliage, or lateral width leaf canopy of the crop row, as observed by sensors or input data entered by an operator of the sprayer vehicle 61. Although FIG. 5 shows right nozzles (222R, 224R, 226R) in a vertical array, in alternate embodiments they may be in a substantially horizontal array, a diagonal array, or any other spatial relationship with each other so long as each discharges crop input, via a corresponding spray zone (e.g., spray zones, 75, 77 and 79), directed toward the right first zone 432R, right second zone 434R and right third zone 436R. Similarly, in alternate embodiments, the left nozzles (222L, 224L, 226L) may be arranged in substantially horizontal array, a diagonal array, or any other spatial relationship with each other such that the crop inputs are directed toward the left first zone 432L, left second zone 434L and left third zone 436L.

As used in this document, the first zone may refer to the left first zone (432L), the right first zone (432R) or both; second zone may refer to the left second zone (434L), the right second zone (434R), or both; the third zone may refer to the left third zone (436L), the right third zone (436R), or both. The zones may be altered by changing the down-tilt angles (431l, 433L, 435L, 431R, 433R, 435R) or other compound angles that define the direction that the crop input leaves each nozzle. For example, the operator can manually reduce the down-tilt of one or more nozzles in the nozzle assembly 60 to treat or spray the foliage of one or more segments of plant rows in accordance with a treatment plan for fungicide, pesticide, insecticide or herbicide.

Figure 6:
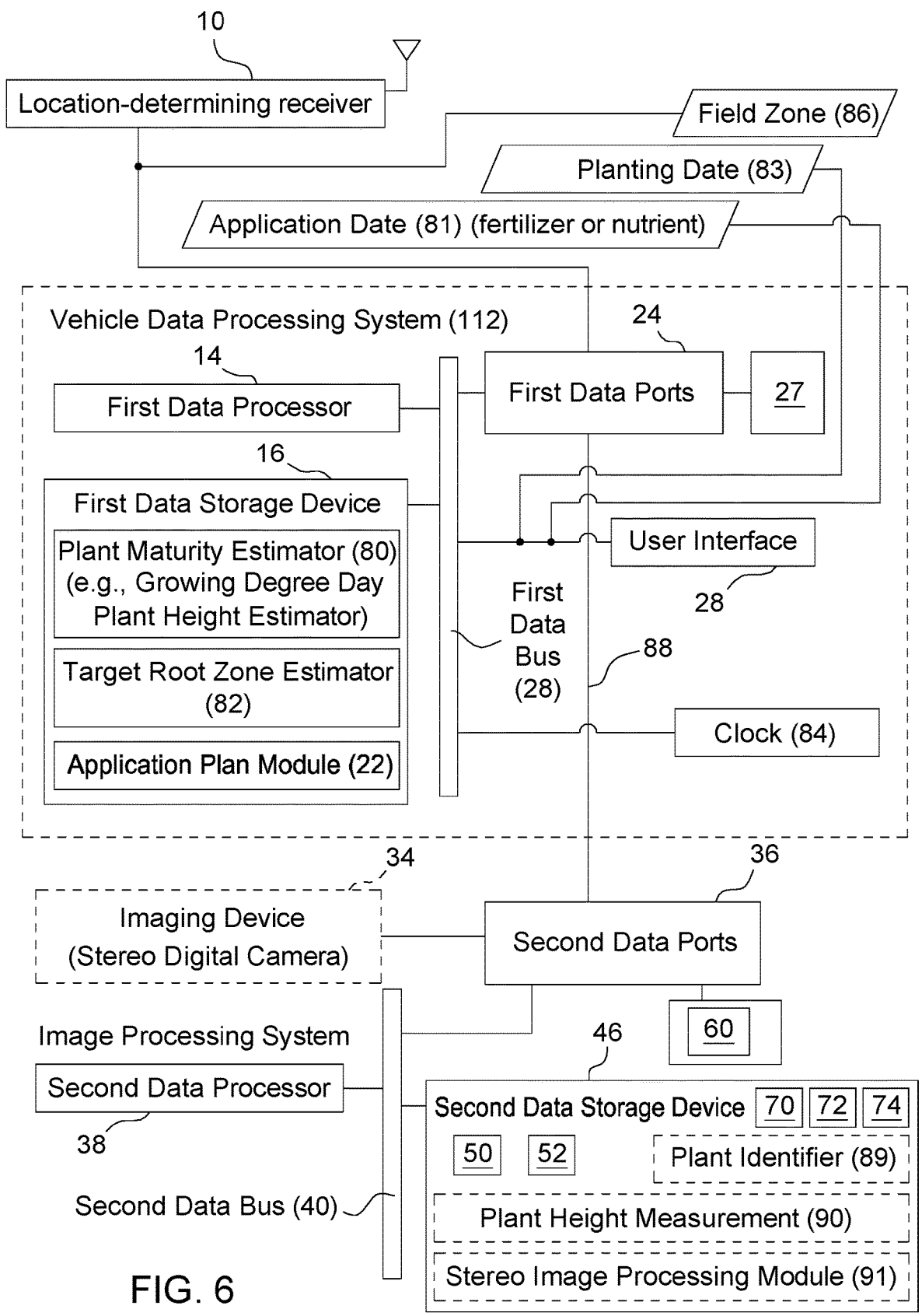
FIG. 6 is an alternate embodiment of a block diagram of a system for spraying plants.

FIG. 6 is an alternate embodiment of a block diagram of a system for spraying plants. The system of FIG. 6 is similar to the system of FIG. 1, except that the vehicle data processing system 12 further comprises plant maturity estimator 80, target root zone estimator 82, and a clock 84, along with the data references to the application date 81, and planting date 83. Like reference numbers in FIG. 1 and FIG. 6 indicate like features or elements.

FIG. 6 further comprises an optional imaging device 34 (e.g., stereo imaging device) and other optional modules related to the imaging device 34, such as a plant identifier 89 module, a plant height measurement 90 module and an image processing module 91 (e.g., stereo image processing module). The imaging device 34 and modules are indicated as optional by the dashed lines and will be described later in this document.

In FIG. 6, the user interface 28 allows the user to enter, download or input information about the planted crop or seeds to establish a planting date 83 for the crop in a particular field. The first data processor 14 receives the input about the planting date 83 from the user interface 28 and the current date from the clock 84 or user interface 28 to estimate the number of days or corresponding maturity state of the planted crop. For example, the plant maturity estimator 80 estimates growing degree days of the crop based on the field zone 86 or agricultural region in which the particular field is located by observing coordinates of the location-determining receiver 10 or user input into the user interface 28 that indicates the field location or field zone 86. As used throughout this document, a growing degree day may refer to a single growing degree day or accumulated growing degree days, such as the sum of growing degree days over a time period or growing season. In one embodiment, the vehicle data processing system 12 may obtain or use the application date 81 of fertilizer or nutrient entered by an operator via the user interface 28. In another embodiment, to enhance the accuracy of the plant maturity estimate determined by the plant maturity estimator 80, the vehicle data processing system 12 or plant maturity estimator 80 may use or obtain local historical precipitation, rainfall, or other historical weather data from commercially available sources accessed through a wireless network, an electronic communications network or on the Internet via a wireless communications device (e.g., wireless transceiver, cellular phone, satellite phone or smartphone) coupled to the first data ports 24.

In one embodiment, the target root zone estimator 82 provides a root zone or target zone for crop inputs at, near or around the plant rows based on one or more of the following plant data: estimated plant height, observed or measured plant height, estimated plant maturity, observed plant maturity, number of plant leaves, estimated drip line of the plant or plant row, estimated lateral width of the plant or row segment, or observed lateral width of the plant or row segment to be treated. For example, in one embodiment, the target root zone estimator 82 provides a recommended zone, among the first zone (432L, 432R), the second zone (434L, 434R) or the third zone (436L, 436R), for each corresponding segment of a plant row consistent with the plant maturity or other plant data output of the plant maturity estimator 80 that is correlated to plant maturity.

In one embodiment, the optional plant identifier module 89, the optional plant height measurement module 90 and a stereo image processing module 91 receive data, such as image data (e.g., stereo image data) of plant rows from the imaging device 34. The optional plant identifier 89 module compares reference images of reference plants or reference foliage stored in the second data storage device 46 or elsewhere to observed images of plants or foliage in one or more plant rows to identify the crop type, species or variety and to estimate the crop maturity. For example, the reference images may comprise plants at various reference growth stages in accordance with established, recognized or generally accepted plant maturity levels. The reference images may be stored in the form of raw images, normalized images, a list of plant parameters, a neural network, or any other suitable format.

In one embodiment, the plant height measurement module 90 estimates a plant height of an observed crop based on collected stereo image data in conjunction with the image processing module 91 (e.g., stereo image processing module). First, the image processing module 91 may use color differentiation to distinguish plant pixels from background images (e.g., soil, sky or weeds) in the collected image data. For example, the second data storage device 46 contains reference plant pixels colors or a reference range of potential plant pixel colors for comparison to collected image data. Second, the image processing module 91 may establish a constellation of plant pixels and a boundary region between plant pixels and background pixels. For example, the boundary region may represent a substantially linear or curved line near at the vertical limit or top of a plant or row. Third, the observed three-dimensional coordinates of the collected image data in the boundary region are converted to real world coordinates to estimate a plant height 266 of plant or segment of a row of plants.

Figure 7A:
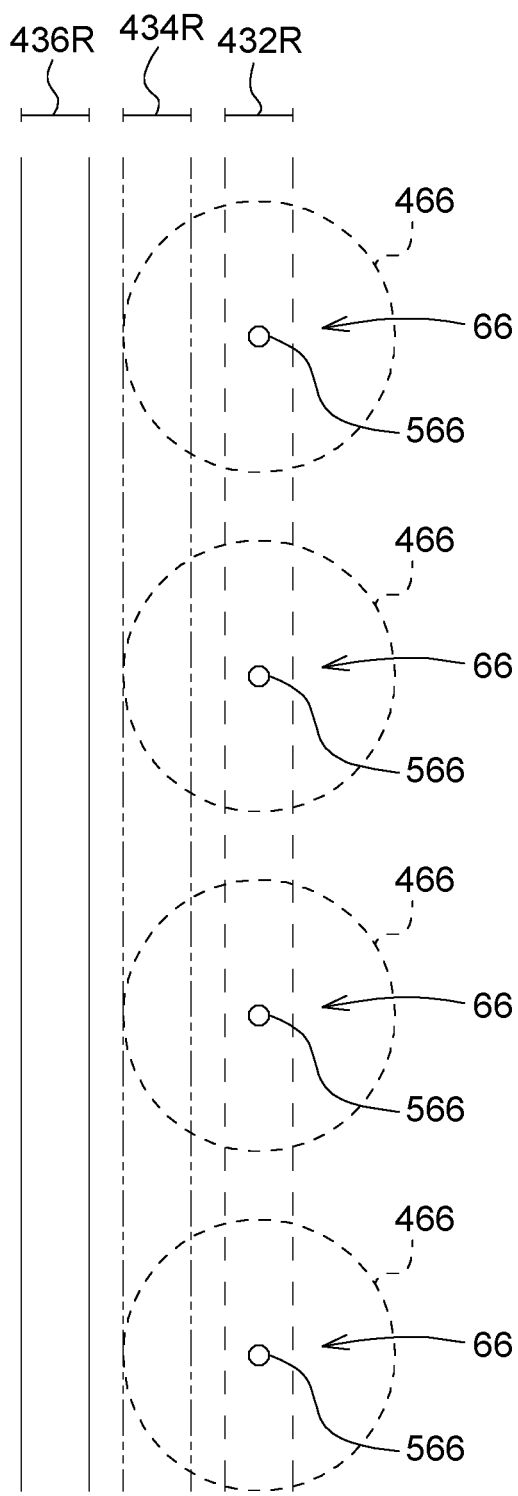
FIG. 7A is a plan view of one illustrative configuration of a row within a field that shows root zones of plants and application zones for crop inputs with respect to the root zones.

FIG. 7A is a plan view of one illustrative configuration of a row of plants 66 within a field that shows root zones 466 of plants 66 and application zones (432R, 434R, 436R) for crop inputs with respect to the root zones 466, which may be commensurate in size with, or proportional to a plant diameter, foliage diameter or leaf canopy diameter. FIG. 7A illustrates the following application zones for crop inputs: a right first zone 432R, a second zone 434R, and a third zone 436R, as strips on the field. As shown, the right first zone 432R is generally parallel to the right second zone 434R and the right third zone 436R. Although the zones in FIG. 7A are shown as mutually exclusive or non-overlapping, in other configurations two or more zones may overlap with each other.

As illustrated in FIG. 7A, the right first zone 432R overlaps with a root zone 466 of one or more plants 66 within a row. In particular, the right first zone 432R intercepts with or overlaps with stalk, stem, trunk or base 566 of one or more plants 66 with a row segment. The right first zone 432R has a longitudinal axis that is aligned with a diameter of the root zone 466 of one or more plants 66 in the row segment.

The right second zone 434R intercepts with or overlaps with a root zone 466 of one or more plants 66 within a row. For example, the right second zone 434R or outer boundary of the right second zone 434R is aligned to intercept with a perimeter of the root zone 466 for each plant 66 within the row segment. In some configurations, the perimeter of root zone 466 may be commensurate with the drip line or width of the plant canopy or foliage width above the root zone 466.

In one illustrative example for carrying out the application plan of crop inputs consistent with FIG. 7A, the implement data processing system 42 or nozzle control module 50 may command or instruct the nozzle assembly 60 to activate (via actuator(s)) one or more nozzles directed toward the right second zone 434R or the right first zone 432R for plants that are greater than a threshold maturity level (e.g., greater than a V5 maturity level for maize or corn, such as a V5 to VT maturity level). As illustrated in FIG. 7A, the right third zone 436R is spaced apart from the right second zone 434R is generally parallel to the right second zone 434R by a lateral gap or safety gap to avoid over-applying or overdosing one or more plants with fertilizer, such as plants that are equal to or less than threshold maturity level (e.g., less than V5 maturity level, such as a V5 to VE maturity for maize or corn plants). For example, the implement data processing system 42 or nozzle control module 50 may command or instruct the nozzle assembly 60 to activate (via actuator(s)) one or more nozzles direct toward the right third zone 436R to avoid damage to immature plants that are equal to or less than the threshold maturity level (e.g., less than V5 maturity level, such as a V5 to VE maturity for maize or corn plants).

Figure 7B:
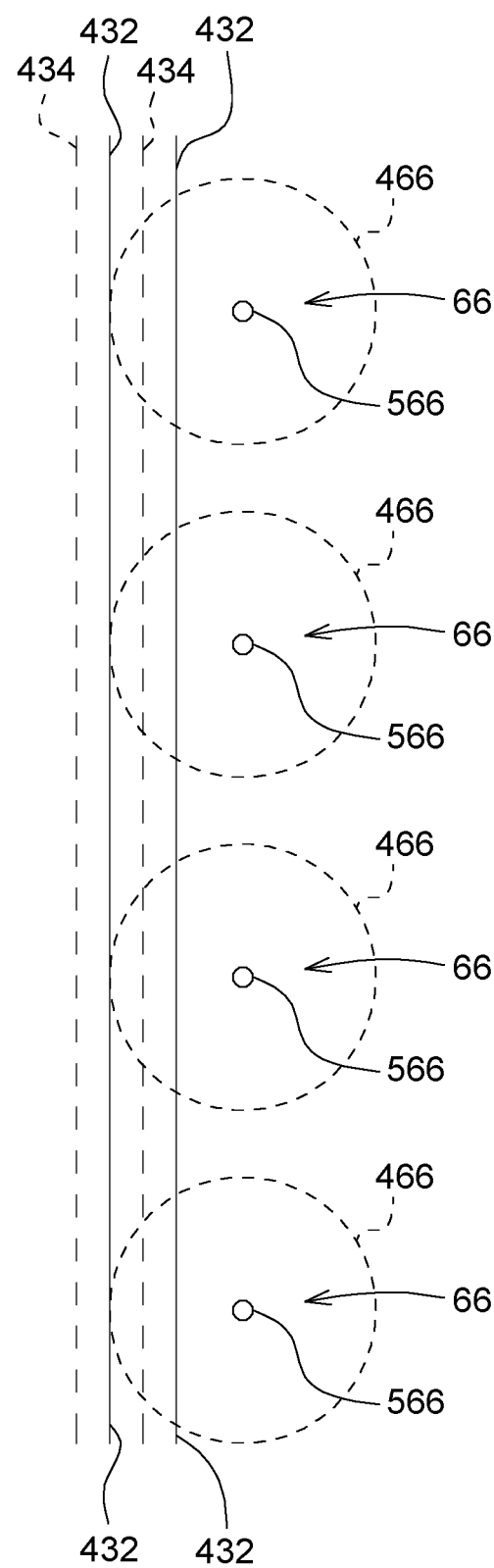
FIG. 7B is a plan view of another illustrative configuration of a row within a field that shows root zones or foliage diameter of plants and application zones for crop inputs with respect to the root zone.

FIG. 7B is a plan view of another illustrative configuration of a row within a field that shows root zones of plants and application zones for crop inputs with respect to the root zone. The plan view in FIG. 7B is similar to the plan view in FIG. 7A, except the application zones, the right first zone 432 and the right second zone 434, comprise overlapping strips. As illustrated, the outer boundary of the right first zone 432 intercepts a perimeter of the root zone 466 of one or more plants 66 in a row. Meanwhile, a centerline axis of the right second zone 434 substantially intercepts the perimeter of one or more root zones 466. In some configurations, the perimeter of root zone 466 may be commensurate with the drip line or width of the plant canopy, where the stem 566 extends from the root zone 466 to the plant canopy.

In one illustrative example for carrying out the application plan of crop inputs consistent with FIG. 7B, the implement data processing system 42 or nozzle control module 50 may command or instruct the nozzle assembly 60 to activate one or more nozzles (via actuator(s)) directed toward the right second zone 432, the right first zone 434, or both for plants that are greater than a threshold maturity level (e.g., greater than a V5 maturity level for maize or corn, such as a V5 to VT maturity level).

Figure 7C:
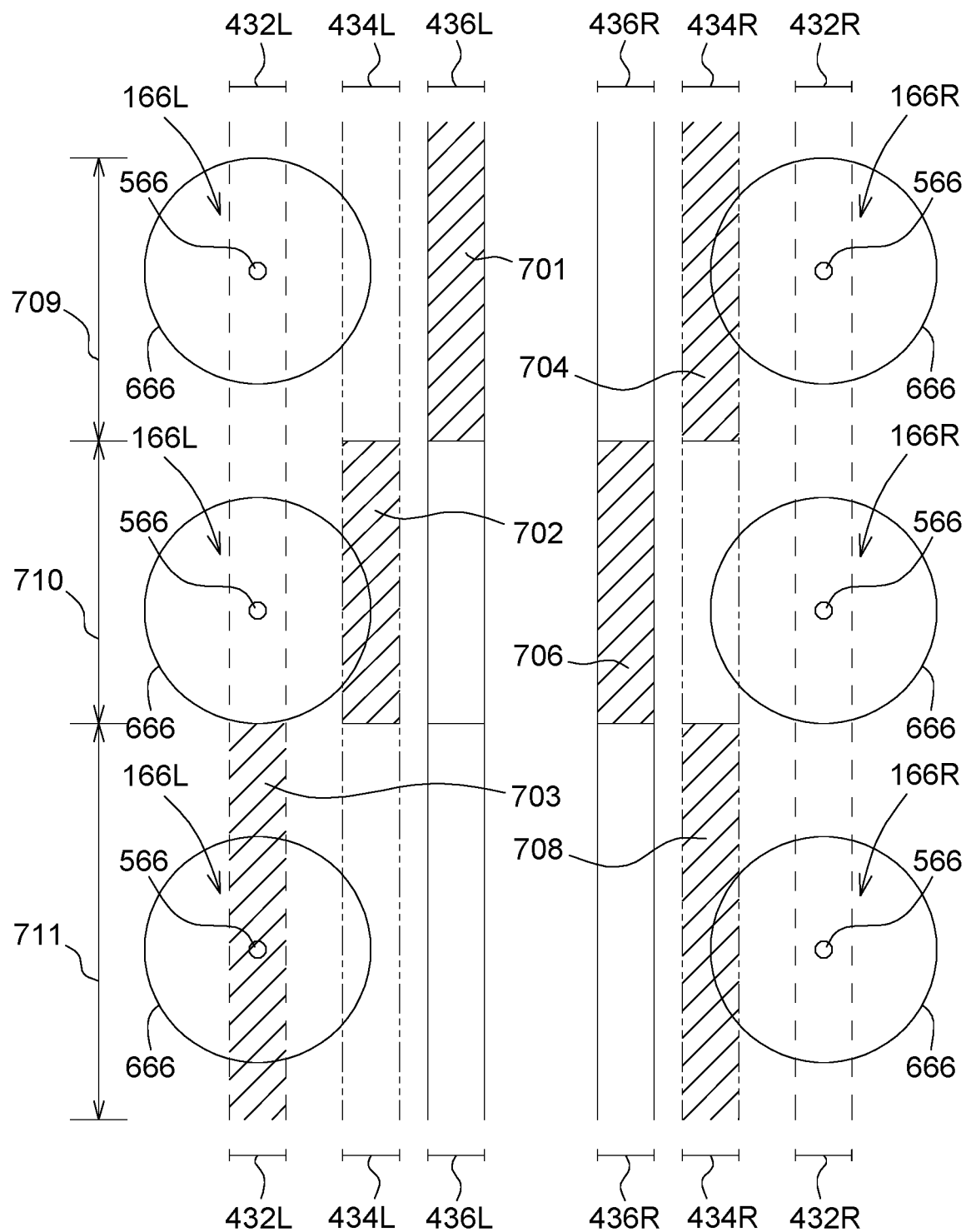
FIG. 7C is a plan view of two adjacent rows within a field that shows root zones or foliage diameter of plants and which application zone(s) for crop inputs are selected for each crop row segment of a row.

FIG. 7C is a plan view of two adjacent rows of plants (166R, 166L) within a field that shows root zones or commensurate foliage diameters 666 of plants (166R, 166L) and which application zone(s) for crop inputs are selected for each crop row segment of a row. As illustrated in FIG. 7C, the left first zone 432L overlaps with a respective root zone or foliage diameter 666 of one or more left plants 166L within a left row and the right first zone 432R overlaps with a respective root zone or foliage diameter 666 of one or more right plants 166R within a right row. In particular, the left first zone 432L and right first zone 434R intercept with or overlap with stalk, stem, trunk or base 566 of one or more plants with each row segment. The left first zone 432L and the right first zone 432R have a longitudinal axis that is aligned with a diameter of the respective foliage diameter 666 or root zone of one or more plants in each row segment.

The left second zone 434L intercepts with or overlaps with a respective foliage diameter 666 or root zone of one or more left plants 166L within a left row and the right second zone 434R intercepts with or overlaps with a respective foliage diameter 666 or root zone of one or more right plants 166R within the right row. For example, the left second zone 434L or outer boundary of the left second zone 434L is aligned to intercept with a perimeter of the respective foliage diameter 666 or root zone for each plant within each row segment. Similarly, the right second zone 434R or outer boundary of the right second zone 434R is aligned to intercept with a perimeter of the respective foliage diameter 666 or the root zone for each plant within each row segment. In some configurations, the perimeter of root zone may be commensurate with or substantially equal the drip line, width of the plant canopy, or foliage diameter 666.

The right third zone 436R is spaced inward from the right plant row 166R and the right second zone 434R. Similarly, the left third zone 426L is spaced inward from the left plant row 166L and the left second zone 434L. As illustrated, the right third zone 436R and the left third zone 436L are strips that are substantially parallel to the right second zone 434R and left second zone 434L, respectively.

The left plant row 166L and the right plant row 166R are divided into three row segments (709, 710, 711), where each row segment (709, 710, or 711) has a longitudinal length, such as a longitudinal length in the direction of travel of a sprayer vehicle. In FIG. 7C, the second data processor 38 or the nozzle control module 50 is adapted to activate one or more nozzles of a nozzle assembly 60 to produce or cover the exemplary patterns indicated by the cross-hatched regions (701, 702, 703, 704, 706, 708) of the left first zone 432L, left second zone 434L, left third zone 436L, right first zone 432R, right second zone 434R, and right third zone 436R. Although only one zone (432L, 434L, 436L) is activated for each corresponding left row region (701, 702, 703) or segment in FIG. 7C, in practice one or more zones (432L, 434L, 436L, 432R, 434R, 436R) may be active for each corresponding left row segment and right row segment. For example, for the first row segment 709, the second data processor 38 or the nozzle control module 50 activates the nozzle assembly 60 to cover the left third zone 436L and the right second zone 434R; for the second row segment 710, the second data processor 38 or the nozzle control module 50 activates the nozzle assembly 60 to cover the left second zone 434L and the right third zone 435R; for the third row segment 711, the second data processor 38 or the nozzle control module 50 activates the nozzle assembly 60 to cover the left first zone 432L and the right second zone 434R. The target zone estimator 80 and application plan module 22 may determine the application zones (e.g., within the illustrative example of FIG. 7C) based on estimated plant maturity, estimated plant height, plant height measurement data 90, growing degree days data (e.g., accumulated growing degree data), or other location specific data of the plants as the vehicle progresses through the rows of the field to avoid damage and provide targeted level of nutrients on a site-specific or plant-specific basis within each row segment (709, 710, 711).

Figure 12:
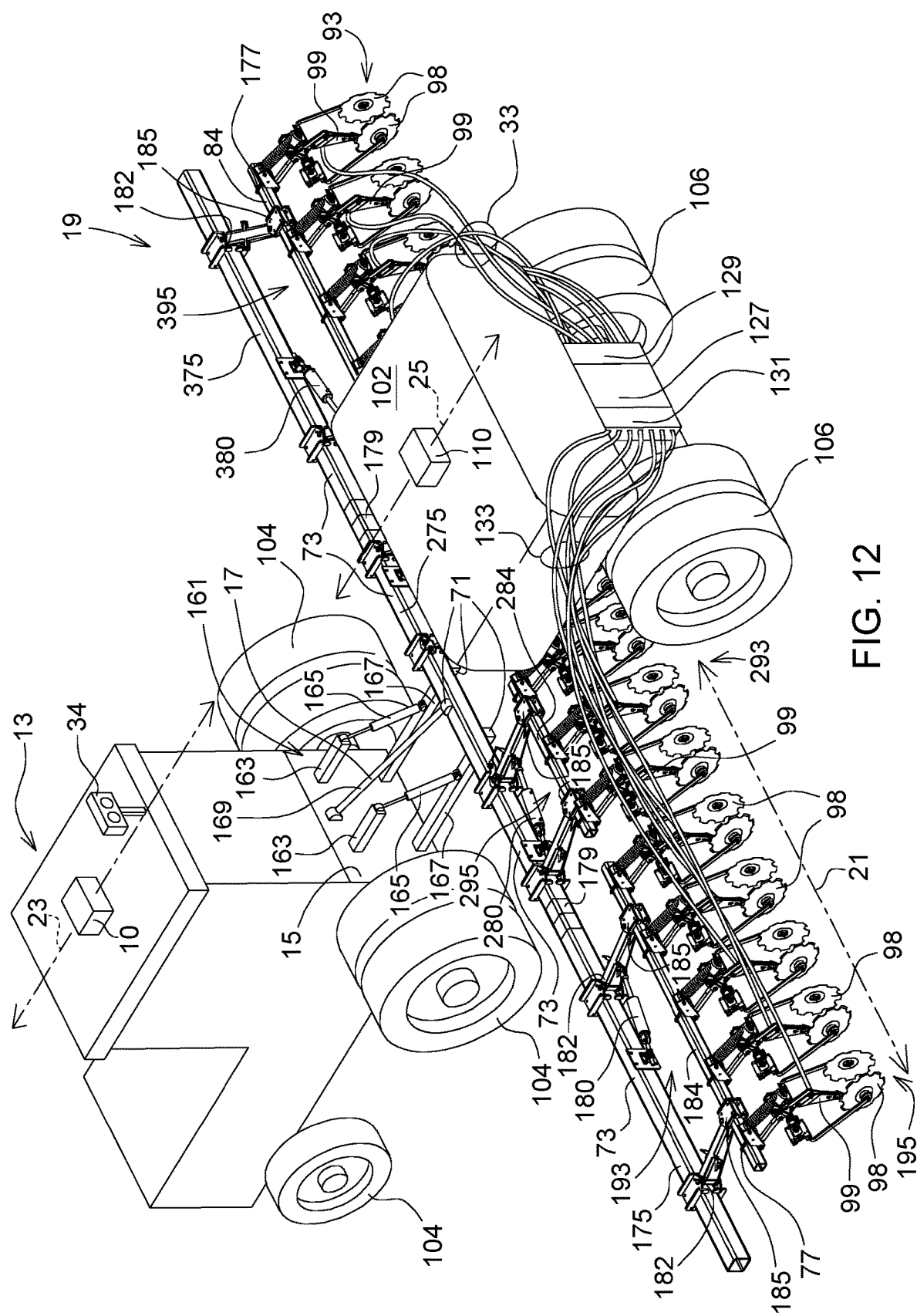
FIG. 12 is a perspective view of a tractor that pulls an implement for applying fertilizer (e.g. anhydrous ammonia) via laterally adjustable nutrient knives or cutters.
Figure 16:
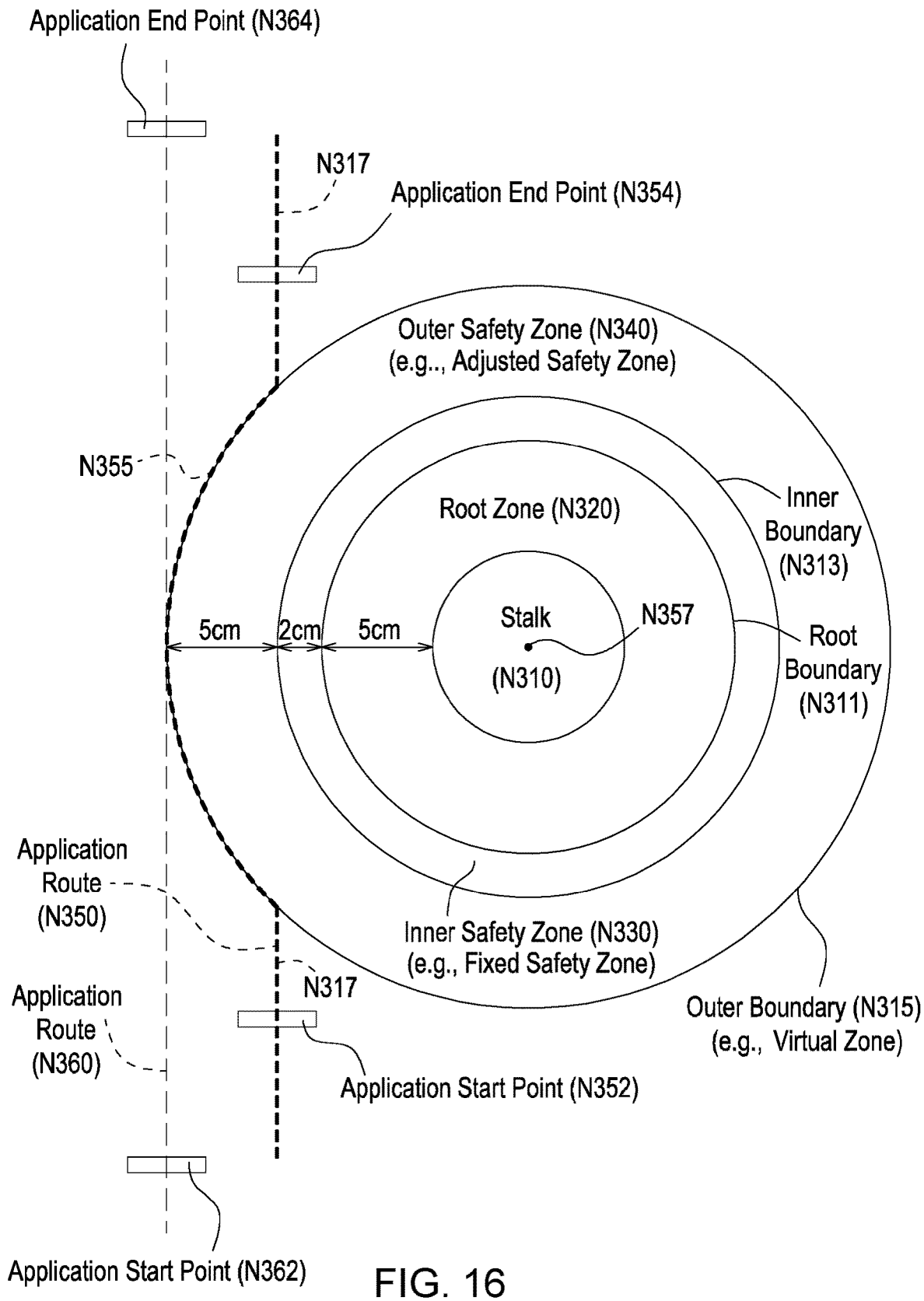
FIG. 16 is a plan view of a nutrient knife path plan or route plan for treating or applying nutrients to plants.

In an alternate embodiment, FIG. 7C may be modified for use in conjunction with the nutrient application system of FIG. 12. For example, the nutrient knifes 99 of FIG. 16 are spaced laterally apart from root zones of each plant (166R, 166L) by a lateral clearance (distance) based on plant height measurement data 90 (or stereo image data from the imaging device 34, or estimated plant maturity data from the plant maturity estimator 80) within each row segment (709, 710, 711), where the lateral clearance prevents damage to the roots within the root zone. Accordingly, the data processor (s) (14, 38) of FIG. 12 controls actuators (180, 280, 380) on a row segment by row segment basis based on plant height measurement data 90 (or stereo image data from the imaging device 34, or estimated plant maturity data from the plant maturity estimator 80) for each respective row segment (709, 710, 711).

FIG. 8 is a flow chart of one embodiment of a method for applying nutrients to plants. The flow chart of FIG. 8 begins in step S801.

In step S801, the first data processor 14 or the plant maturity estimator 80 determines a growth state or maturity state of a plant (66, 166L, 166R) or plant row segment based on a planting date, a current date and the crop type of the plant. For example, the plant maturity estimator 80 may subtract the planting date of the plant from the current date to estimate one or more of the following: growing days, growing degree days (e.g., accumulated growing degree days), plant height, stem or base diameter, and plant maturity.

Step S801 may be carried out by various techniques, which may be applied separately or cumulatively. Under a first technique, the growing degree days may be used to estimate plant height or plant maturity for a particular crop. Under a second technique, the first data processor 14 or the plant maturity estimator 80 determines accumulated growing degree days by adding the sum of growing degree days over a growing duration, where each individual growing degree day (in the sum) is determined by subtracting a reference temperature for a particular plant type, species or variety (e.g., corn or soybeans) from an average daily temperature for the corresponding day. Under a third technique, the first data processor 14 or the plant maturity estimator 80 estimates growth state or the plant maturity based on growing degree days derived from temperature data for the geographic area associated with the plant, the planting date, the current date and the crop type of the plant. Under a fourth technique, the first data processor 14 or the plant maturity estimator 80 may receive or obtain precipitation data (e.g., rainfall), sunlight data, temperature data, and growing days (e.g., via the user interface 28 or online commercially available data sources) to estimate plant maturity in accordance with a plant maturity estimator module 80 for particular crop in a corresponding geographic area.

Under a fifth technique, the first data processor 14 or the plant maturity estimator 80 adjusts the determined growth state or maturity state for the plant based on collected stereo image data predominating over the derived growing degree days, where the imaging system 34 collects stereo image data on the plant to evaluate a plant size or plant height to verify the determined growth state or maturity state for the plant. In alternate embodiments, the imaging system 34 may comprise a monocular imaging device, a laser scanner, a LIDAR (light detection and ranging) device, a laser range finder, or another suitable sensor for estimating the plant size, width, volume or height of one or more plants.

Under a sixth technique, the first data processor 14 or the plant maturity estimator 80 adjusts the determined growth state or maturity state, where the height sensor 32 or imaging system 34 collects observed plant height data on the plant to verify the determined growth state of maturity state for the plant. For example, the first data processor 14 or the plant maturity estimator 80 adjusts the determined growth state or maturity state for the plant based on the observed plant height predominating of the derived growing degree days.

Under a seventh technique, the first data processor 14 or the plant maturity estimator 80 estimates the growth state or plant maturity is based on a growth model that uses a historic mean, average or median precipitation for the location of the plant, the planting date, the current date and the crop type of the plant.

Under an eighth technique, the first data processor 14 or the plant maturity estimator 80 estimates the growth state or plant maturity is based on observed rainfall or precipitation for the field or region associated with the plant.

In step S802, the first data processor 14 or target root zone estimator 82 estimates the root size, root radius, root diameter of the root zone 466 of the plant (66, 166L, 166R) or plant row segment based on the determined plant maturity or grow state.

In an alternate embodiment, the first data processor 14 or target root zone estimator 82 estimates the root size, root radius, root diameter of the root zone (e.g., 466) of the plant (66, 166L, 166R) or plant row segment based on the determined plant maturity or grow state.

In step S803, the second data processor 38 or nozzle control module 50 adjusts a lateral offset of the spray pattern (75, 77, 79) of a nozzle assembly 60 based on the estimated root size, root radius, root diameter (e.g., of the root zone 466) to target alignment or maximization of overlap area of a strip (e.g., first zone (432L, 432R), second zone (434L, 434R) or third zone (436L, 436R)) of the spray pattern (75, 77, 79) with the corresponding root zone (e.g., 466)).

Step S803 may be accomplished in accordance with one or more techniques, which may be applied separately or individually. Under a first technique, the lateral offset of the spray pattern (75, 77, 79) may be based on the lateral offset of the nozzle assembly 60 from a centered row position with respect to the right plant row 166R, the left plant row 166L, or both as measured or observed by one or more distance sensors (30, 130L, 130R). In turn, the plant proximity processing module 52 may interpret or filter (e.g., average) the observed lateral offset (from the centerline of the row, as determined by a location-determining receiver (10 or 110)) of the nozzle assembly 60 from the distance sensors (30, 130L, 130R) for each respective row segment (e.g., 709, 710, 711) or interval.

Under a second technique, the nozzle control module 50 or second data processor 38 activates one or more left nozzles (222L, 224L, 226L) of the nozzle assembly 60 to direct crop input differently for each left row segment (709, 710, 711 in FIG. 7C) toward any permutation of a left first zone 432L, a left second zone 434L or a left third zone 436L based on the maturity level of one or more left plants 166L in the left row segment (709, 710, 711) and a lateral offset to a center point between adjacent row segments.

Under a third technique, the nozzle control module 50 or second data processor 38 activates one or more right nozzles (222R, 224R, 226R) of the nozzle assembly 60 to direct crop input differently for each right row segment (709, 710, 711 in FIG. 7C) toward a right first zone 432R, a right second zone 434R or a right third zone 436R based on the maturity level of one or more right plants 166R in the right row segment and a lateral offset to a center point between adjacent row segments.

FIG. 9 is a flow chart of another embodiment of a method for applying nutrients to plants. Like reference numbers in FIG. 8 and FIG. 9 indicate like steps or procedures.

In step S801, the first data processor 14 or the plant maturity estimator 80 determines a growth state or maturity state of a plant (66, 166L, 166R) or plant row segment based on a planting date, a current date and the crop type of the plant. For example, the plant maturity estimator 80 may subtract the planting date of the plant from the current date to estimate one or more of the following: growing days, growing degree days, plant height, stem or base diameter, and plant maturity.

Step S801 may be carried out by various techniques, which may be applied separately or cumulatively. Under a first technique, the growing degree days may be used to estimate plant height or plant maturity for a particular crop. Under a second technique, the first data processor 14 or the plant maturity estimator 80 determines growing degree days by subtracting a reference temperature for a particular plant type, species or variety (e.g., corn or soybeans), from an average daily temperature for a growing duration. Under a third technique, the first data processor 14 or the plant maturity estimator 80 estimates growth state or the plant maturity based on growing degree days derived from temperature data for the geographic area associated with the plant, the planting date, the current date and the crop type of the plant. Under a fourth technique, the first data processor 14 or the plant maturity estimator 80 may receive or obtain precipitation data (e.g., rainfall), sunlight data, temperature data, and growing days (e.g., via the user interface 28 or online commercially available data sources) to estimate plant maturity in accordance with a plant maturity estimator module 80 for particular crop in a corresponding geographic area.

Under a fifth technique, the first data processor 14 or the plant maturity estimator 80 adjusts the determined growth state or maturity state for the plant based on collected stereo image data predominating over the derived growing degree days, where the imaging system 34 collects stereo image data on the plant to evaluate a plant size or plant height to verify the determined growth state or maturity state for the plant.

Under a sixth technique, the first data processor 14 or the plant maturity estimator 80 adjusts the determined growth state or maturity state, where the height sensor 32 or imaging system 34 collects observed plant height data on the plant to verify the determined growth state of maturity state for the plant. For example, the first data processor 14 or the plant maturity estimator 80 adjusts the determined growth state or maturity state for the plant based on the observed plant height predominating of the derived growing degree days.

Under a seventh technique, the first data processor 14 or the plant maturity estimator 80 estimates the growth state or plant maturity is based on a growth model that uses a historic mean, average or median precipitation for the location of the plant, the planting date, the current date and the crop type of the plant.

Under an eighth technique, the first data processor 14 or the plant maturity estimator 80 estimates the growth state or plant maturity is based on observed rainfall or precipitation for the field or region associated with the plant.

In step S802, the first data processor 14 or target root zone estimator 82 estimates the root size, root radius, root diameter of the root zone 466 of the plant (66, 166L, 166R) or plant row segment based on the determined plant maturity or grow state.

In an alternate embodiment, the first data processor 14 or target root zone estimator 82 estimates the root size, root radius, root diameter of the root zone (e.g., 466) of the plant (66, 166L, 166R) or plant row segment based on the determined plant maturity or grow state.

In step S803, the second data processor 38 or nozzle control module 50 adjusts a lateral offset of the spray pattern (75, 77, 79) of a nozzle assembly 60 based on the estimated root size, root radius, root diameter (e.g., of the root zone 466) to target alignment or maximization of overlap area of a strip (e.g., first zone (432L, 432R), second zone (434L, 434R) or third zone (436L, 436R)) of the spray pattern (75, 77, 79) with the corresponding root zone (e.g., 466)). For example, the lateral offset of the spray pattern may be based on the lateral offset of the nozzle assembly from a centered row position with respect to the right plant row 166R, the left plant row 166L, or both as measured or observed by one or more distance sensors (30, 130L, 130R). In turn, the plant proximity processing module 52 may interpret or filter (e.g., average) the observed lateral offset (from the centerline of the row, as determined by a location-determining receiver (10 or 110)) of the nozzle assembly 60 from the distance sensors (30, 130L, 130R) for each respective row segment (e.g., 709, 710, 711) or interval.

In step S804, an imaging device 34 (e.g., stereo imaging digital camera) collects stereo image data on the plant to evaluate a plant size or plant height to verify the determined grow state or maturity state for the plant or row segment of plants.

In step S805, the first data processor 14 or the plant maturity estimator 80 determines or adjusts a grow state or maturity state for the plant based on the collected stereo image data (e.g., or associated plant height derived from the stereo image data) predominating over requisite growing degree days (or maturity derived from a maturity model based on observed growing time, precipitation data, sunlight data, and temperature data for the growing area) estimated based on the planting date, the current date and crop type. In an alternate embodiment, plant maturity data could be determined from a plant image (e.g., corn plant image) collected by an imaging device 34 or by counting leaves or measuring (e.g., integrating over) vegetation spatial area or volume. The imaging device 34 can facilitate counting of leaves or measuring vegetation volume based on optics and geometry information.

FIG. 10 is a flow chart of yet another embodiment of a method for applying nutrients to plants. Like reference numbers in FIG. 9 and FIG. 10 indicate like steps or procedures.

Step S801 may be carried out by various techniques, which may be applied separately or cumulatively. Under a first technique, the growing degree days may be used to estimate plant height or plant maturity for a particular crop. Under a second technique, the first data processor 14 or the plant maturity estimator 80 determines growing degree days by subtracting a reference temperature for a particular plant type, species or variety (e.g., corn or soybeans), from an average daily temperature for a growing duration. Under a third technique, the first data processor 14 or the plant maturity estimator 80 estimates growth state or the plant maturity based on growing degree days derived from temperature data for the geographic area associated with the plant, the planting date, the current date and the crop type of the plant. Under a fourth technique, the first data processor 14 or the plant maturity estimator 80 may receive or obtain precipitation data (e.g., rainfall), sunlight data, temperature data, and growing days (e.g., via the user interface 28 or online commercially available data sources) to estimate plant maturity in accordance with a plant maturity estimator module 80 for particular crop in a corresponding geographic area.

Under a fifth technique, the first data processor 14 or the plant maturity estimator 80 adjusts the determined growth state or maturity state for the plant based on collected stereo image data predominating over the derived growing degree days, where the imaging system 34 collects stereo image data on the plant to evaluate a plant size or plant height to verify the determined growth state or maturity state for the plant.

Under a sixth technique, the first data processor 14 or the plant maturity estimator 80 adjusts the determined growth state or maturity state, where the height sensor 32 or imaging system 34 collects observed plant height data on the plant to verify the determined growth state of maturity state for the plant. For example, the first data processor 14 or the plant maturity estimator 80 adjusts the determined growth state or maturity state for the plant based on the observed plant height predominating of the derived growing degree days.

Under a seventh technique, the first data processor 14 or the plant maturity estimator 80 estimates the growth state or plant maturity is based on a growth model that uses a historic mean, average or median precipitation for the location of the plant, the planting date, the current date and the crop type of the plant.

Under an eighth technique, the first data processor 14 or the plant maturity estimator 80 estimates the growth state or plant maturity is based on observed rainfall or precipitation for the field or region associated with the plant.

In step S802, the first data processor 14 or target root zone estimator 82 estimates the root size, root radius, root diameter of the root zone 466 of the plant (66, 166L, 166R) or plant row segment based on the determined plant maturity or grow state.

In an alternate embodiment, the first data processor 14 or target root zone estimator 82 estimates the root size, root radius, root diameter of the root zone (e.g., 466) of the plant (66, 166L, 166R) or plant row segment based on the determined plant maturity or grow state.

In step S803, the second data processor 38 or nozzle control module 50 adjusts a lateral offset of the spray pattern of a nozzle assembly 60 based on the estimated root size, root radius, root diameter (e.g., of the root zone 466) to target alignment or maximization of overlap area of a strip of the spray pattern with the corresponding root zone (e.g., 466). For example, the lateral offset of the spray pattern (75, 77, 79) may be based on the lateral offset of the nozzle assembly 60 from a centered row position with respect to the right plant row 166R, the left plant row 166L, or both as measured or observed by one or more distance sensors (30, 130L, 130R). In turn, the plant proximity processing module 52 may interpret or filter (e.g., average) the observed lateral offset (from the centerline of the row, as determined by a location-determining receiver (10 or 110)) of the nozzle assembly 60 from the distance sensors (30, 130L, 130R) for each respective row segment (e.g., 709, 710, 711) or interval.

In step S806, the second data processor 38 or the nozzle control module 50 selectively activates one or more directional nozzles of the nozzle assembly 60 to adjust the lateral offset of the spray pattern based on the root size, or root radius of the root zone (e.g., 466) to target alignment or maximization of overlap area of an application zone (e.g., strip) of the spray pattern with corresponding root zone (e.g., 466).

FIG. 11 is a flow chart of still another embodiment of a method for applying nutrients to plants. The method of FIG. 11 begins in step S800.

In step S800, a plant height sensor (30, 130L, 130R) detects an observed plant height of a sample plant or plants (66, 166L, 166R) in one or more rows of a crop.

In step S805, the first data processor 14 or the plant maturity estimator 80 determines a grow state or maturity state of a plant (66, 166R, 166L) based on the observed plant height 266 or an average, mean, mode or other derived plant height for a plant, a plant row segment, or a field.

In step S802, the first data processor 14 or target root zone estimator 82 estimates the root size or root radius of the root zone 466 of the plant based on the determined plant maturity or grow state (or observed plant height 266). However, in an alternate embodiment, the first data processor 14 or target zone estimator 20 may estimate the root size or root radius of the root zone of the plant based on the observed plant height 266 or the derived plant height for a plant, a plant row segment, or a field.

In step S803, the second data processor 38 or nozzle control module 50 adjusts a lateral offset of the spray pattern of a nozzle assembly 60 based on the root size, root radius, root diameter of the root zone (e.g., 466) to target alignment or maximization of overlap area of an application zone (e.g., strip) of the spray pattern (75, 77, 79) to direct a crop input (e.g., nutrients or chemicals) to a strip or zone with respect to the corresponding root zone. The lateral offset of the spray pattern may be based on the lateral offset of the nozzle assembly from a centered row position with respect to the right plant row 166R, the left plant row 166L or both as measured or observed by one or more distance sensors. In turn, the plant proximity processing module may interpret or filter (e.g., average) the observed lateral offset of the nozzle assembly 60 from the distance sensors (30, 130L, 130R) for each respective row segment (709, 710, 711) or interval.

FIG. 12 is a perspective view of a tractor that pulls an implement for applying fertilizer (e.g. anhydrous ammonia) via laterally adjustable nutrient knives or cutters. FIG. 12 is perspective rear view of a vehicle 13 towing one embodiment of a ground-engaging implement 19 with lateral position adjustment along, or parallel to, lateral axis 21 to apply crop inputs (e.g., ammonia) with an adjustable lateral offset with respect to one or more plant rows, seed beds, drip tape, irrigation lines, reference lines or curves. The lateral axis 21 is substantially perpendicular to the vehicle longitudinal axis 23 of the vehicle, the implement longitudinal axis 25 of the implement 19, or both.

FIG. 12 shows that the ground-engaging implement 19 has a tank 102 for holding crop inputs, such as chemicals, nutrients, fertilizer, ammonia, nitrogen, potassium, phosphorus, minerals or other crop inputs. In an alternate embodiment, the crop inputs may include fungicide, pesticide, herbicide, miticide, or other crop treatments. In one embodiment, a sprayer pump 127 accepts an input of a crop input and pumps the crop input via a first manifold 129 and tubes 133 to a group of corresponding first nozzles or first nutrient knives 99 for application to crop rows of plants; similarly, the sprayer pump 127 accepts an input of a crop input and pumps the crop input via a second manifold 131 and tubes 133 to a group of corresponding second nozzles and second nutrient knives 99 for application to crop rows of plants. In another configuration, the tank 102 may contain pressurized ammonia, anhydrous ammonia, or another pressurized crop input that has pressure greater than atmospheric pressure such that the sprayer pump 27 is not required, where the tank 102 directly feeds a first manifold 29, a second manifold 131, and where the first manifold 129 and the second manifold 131 may be associated with pressure regulator to regulate the pressure and flow of the pressurized crop input.

In one embodiment, a ground-engaging agricultural implement 19 comprises a front member 73 for coupling to a hitch 161. The front member 73 comprises a multi-sectioned foldable member that includes multiple sections. In one embodiment, the front member 73 comprises set of hinged sections that can be folded upward, wherein a central one (e.g., third front member 275) of the hinged sections is associated with a hitch 161 for attachment to a vehicle for pulling or towing the implement. For example, the front member 73 comprises a first front member 375 (e.g., first section), a second front member 175 (e.g., second section) and a third front member 275 (e.g., third section). The first, second and third front members (75, 175, 275) may be hinged at joints or hinges 79 to allow the first front member 375 and the second front member 175 to fold upward with respect to the third front member 275 (e.g., central member) and inward toward the implement longitudinal axis 25 for transportation.

In one embodiment, a set of rear members 77 are associated with the front member 73, which comprises the first front member 375, the second front member 175 and the third front member 275. For example, the rear members 77 comprise a first rear member 84 associated with one or more corresponding first row units 93, a second rear member 184 associated with one or more second row units 193, and a third rear member 284 associated with one or more corresponding third row units 293.

The ground engaging-implement 19 may be regarded as a set of trapezoidal sections (395, 195, 295) or parallelogram sections, where each section is formed by a segment or portion of the front member 73, a segment or portion of the rear member 77, and a pair pivotable arms that pivotally interconnect the segment of the front member 73 and the rear member 77. Although FIG. 12 illustrates three trapezoidal sections (e.g., substantially parallelogram sections), any number of trapezoidal sections greater than two may be used.

First Trapezoidal Section

With respect to a first trapezoidal section 395, a first rear member 84 is spaced apart from a segment or portion of the front member 73 and positioned generally parallel to a segment or portion of front member 73. For example, a first rear member 84 is spaced apart from a first front member 375 and positioned generally parallel to the first front member 375. A first pair of first pivotable arms 76 are generally parallel to each other. The first pair of first pivotable arms 76 are rotatably connected to the front member 73 or first front member 375 at two front pivot points 182. The first pair of first pivotable arms 76 are rotatably connected to the first rear member 84 at two rear pivot points 185. The first front member 375, first pivotable arms 76 and the first rear member 84 collectively form a pivotable, trapezoidal structure (e.g., parallelogram structure) that permits the first rear member to move along or parallel to the lateral axis 21, which allows the opener (e.g., nutrient knife 99) or first row units 93 to be laterally adjusted as the vehicle 13 traverses a path, swath, a set of plant rows, a set of seed rows, or planted seedbeds.

At least one first opener (e.g., nutrient knife 99 or projecting, ground-engaging member) extends downward from or with respect to the first rear member 84. A first actuator 180 has a first end and a second end opposite the first end. The first end is coupled to one of the first pivotable arms 76. The second end is coupled to the front member 73 or first front member 375 to adjust the lateral position of the first row unit 93, the first opener (e.g., nutrient knife 99). The first actuator 180 increases or decreases the distance or span between the first end and the second end to adjust the lateral position, such as the lateral position of the first rear member 84 with respect to the first front member 375. A first position sensor 168 is arranged to estimate a lateral position of the first row unit 93 with respect to the implement longitudinal axis 25 or any reference point on or associated with the front member 73, or the lateral position of the first opener (e.g., nutrient knife 99) with respect to the implement longitudinal axis 25 or any reference point on or associated with the front member 73. For example, the first position sensor 181 can estimate the lateral position based on an angle between any first pivotable arm 76 and the first front member 375 or the first rear member 84. Each nutrient knife 99 or opener that opens a furrow or groove in the soil for insertion of fertilizer, anhydrous ammonia, nitrogen or other crop input is followed by a closer 98 to covers the furrow or groove, and any associated crop input. For example, as illustrated the closer 98 comprises a serrated wheel or disc with a serrated periphery.

Second Trapezoidal Section

In the second trapezoidal section 195, a second rear member 184 is spaced apart from the second front member 175 and positioned generally parallel to the second front member 175. A second pair of second pivotable arms 176 are generally parallel to each other. The second pair of second pivotable arms 176 are rotatably connected to the second front member 175 at two front pivot points 182. The second pair of second pivotable arms 176 are rotatably connected to the second rear member 184 at two rear pivot points 185. The second front member 175, second pivotable arms 176 and the second rear member 184 collectively form a pivotable, trapezoidal structure (e.g., parallelogram structure) that permits the second rear member 184 to move along or parallel to the lateral axis 21, which allows the opener (e.g., nutrient knife 99) or second row units 193 to be laterally adjusted to a second lateral position as the vehicle 13 traverses a path, swath, a set of plant rows, a set of seed rows, or planted seedbeds.

At least one first opener (e.g., nutrient knife 99 or projecting, ground-engaging member) extends downward from or with respect to the second rear member 184. A second actuator 280 has a first end and a second end opposite the first end. The first end is coupled to one of the second pivotable arms 176. The second end is coupled to the front member 73 or first front member 375 to adjust a second lateral position of the second row unit 193, the first opener (e.g., nutrient knife 99).

The second actuator 280 increases or decreases the distance or span between the first end and the second end to adjust the lateral position, such as the lateral position of the second rear member 184 with respect to the second front member 175. A second position sensor 281 is arranged to estimate a second lateral position of the second row unit 193 with respect to the implement longitudinal axis 25 or any reference point on or associated with the front member 73 or the second front member 175; or the lateral position of the first opener (e.g., nutrient knife 99) with respect to the implement longitudinal axis 25 or any reference point on or associated with the front member 73. For example, the second position sensor 281 can estimate the lateral position based on an angle between any second pivotable arm 176 and the second front member 175 or the second rear member 184. Each nutrient knife 99 or opener that opens a furrow or groove in the soil for insertion of fertilizer, anhydrous ammonia, nitrogen or other crop input is followed by a closer 98 to covers the furrow or groove, and any associated crop input. For example, as illustrated the closer 98 comprises a serrated wheel or disc with a serrated periphery.

Third Trapezoidal Section

In the third trapezoidal section 295, a third rear member 284 is spaced apart from the third front member 275 and positioned generally parallel to the third front member 275. A third pair of third pivotable arms 276 are generally parallel to each other. The third pair of third pivotable arms 276 are rotatably connected to the third front member 275 at two front pivot points 182. The third pair of third pivotable arms 276 are rotatably connected to the third rear member 284 at two rear pivot points 185. The third front member 275, third pivotable arms 276 and the third rear member 284 collectively form a pivotable, trapezoidal structure (e.g., parallelogram structure) that permits the third rear member 284 to move along or parallel to the lateral axis 21, which allows the opener (e.g., nutrient knife 99) or third row units 293 to be laterally adjusted to a third lateral position as the vehicle 13 traverses a path, swath, a set of plant rows, a set of seed rows, or planted seedbeds.

At least one first opener (e.g., nutrient knife 99 or projecting, ground-engaging member) extends downward from or with respect to the third rear member 284. A third actuator 380 has a first end and a second end opposite the first end. The first end is coupled to one of the third pivotable arms 276. The second end is coupled to the front member 73 or third front member 275 to adjust the lateral position of the third row unit 293, the first opener (e.g., nutrient knife 99).

The third actuator 380 increases or decreases the distance or span between the first end and the second end to adjust the lateral position, such as the lateral position of the third rear member 284 with respect to the third front member 275. A third position sensor 381 is arranged to estimate a second lateral position of the third row unit 293 with respect to the implement longitudinal axis 25 or any reference point on or associated with the front member 73 or the third front member 275; or the lateral position of the first opener (e.g., nutrient knife 99) with respect to the implement longitudinal axis 25 or any reference point on or associated with the front member 73. For example, the third position sensor 381 can estimate the lateral position based on an angle between any third pivotable arm 276 and the third front member 275 or the third rear member 284.

Further, in one embodiment, the first row units 93, the second row units 193, the third row units 293 and any other row unit can be adjusted laterally and independently of each other. For example, the control system of FIG. 13 can control some row units (e.g., any permutation or combination of 93, 193, 293) to be centered in the rows while other row units are laterally moved to the right or left, and the lateral position of each separately adjustable set of row units can be continuously adjusted based on the implement position of the implement (e.g., as determined by a an implement location-determining receiver (e.g., 110)) in the field to track a path plan, to avoid obstacles, irrigation lines, or drip tape, or to vary the nutrient proximity to plant roots or seeds based on the soil characteristics, seed specifications, seed planting density, seed varieties/coatings, and agronomic prescription plan. Each nutrient knife 99 or opener that opens a furrow or groove in the soil for insertion of fertilizer, anhydrous ammonia, nitrogen or other crop input is followed by a closer 98 to covers the furrow or groove, and any associated crop input. For example, as illustrated the closer 98 comprises a serrated wheel or disc with a serrated periphery.

Hitch

As illustrated in FIG. 12, in one embodiment, a ground-engaging agricultural implement 19 comprises a front member 73, first front member 375 or third front implement member 275 for coupling to a hitch 161. As illustrated the hitch 161 comprises a three-point hitch assembly, although other hitch configurations can be used. In one embodiment, the hitch 161 comprises a pair of lower arms 167 that extend rearwards from a rear 15 of the vehicle 13, a set of upper arms 163 spaced apart from the lower arms 167, where each of the upper arms 163 is coupled to a corresponding lower arm 167 via one or more adjustable hitch hydraulic cylinders 165 that are capable of adjusting the height of the lower arms 167 and a first front member 375 of the implement 19 that is attached to the lower arms 167 at lower hitch points 171. An intermediate arm 17 extends rearwards from the rear of the vehicle via a flexible linkage and is attachable to the first front member 375 an upper hitch point 169.

In FIG. 12, the vehicle 13 (e.g., tractor) comprises a propulsion unit that can drive or power wheels or tracks that can track or traverse over a guidance path or path plan that is aligned with or coextensive with a center point (or any target offset from the center point) between adjacent crop rows, to minimize damage to plants or seeds from the wheels or tires. The guidance path may comprise a linear path segment, a curved path, a contour paths or the combination of any of the foregoing paths. In one embodiment, the vehicle is associated with a vehicle location-determining receiver 34, such as a satellite navigation receiver (e.g., with differential correction of the carrier phase of the signal), to estimate a position of the vehicle 13. The path of the vehicle wheels 104 or tires of the vehicle 13 and the path of the implement wheels 106 of the implement 19 can be guided consistent with intercepting or tracking the guidance path or path plan that is aligned with or coextensive with the center point (or any target offset from the center point) between adjacent crop rows. Meanwhile, the ground-engaging implement 19, or its different row units can be moved to a lateral position that is independent of maintaining the wheels or tires of the tractor or implement 19 between the plant rows.

Instead, the a control system 11 or data processing system can adjust the lateral position of the ground-engaging implement 19 to have an offset with respect to a row of plants or row of seeds such that the crop inputs (e.g., nutrients, fertilizer, or nitrogen) are directed to or dispensed to a target zone (e.g., an intermediate target zone) that is between the center line between adjacent rows and the plant stems, stalk or trunk of the plant row, or seed bed row, drip tape segment, or irrigation segment.

The implement 19 can be equipped with various ground-engaging assemblies or row units. Under a first mode (e.g., nutrient application mode) of operation, row units are designed to apply nitrogen, anhydrous ammonia, fertilizer or other nutrients to rows of plants or seeds that have already been planted. In the first mode, the control system 11 can be provided with as-planted data for the plants or seeds that is based on a location determining receiver, such as a satellite navigation receiver with differential correction, RTK correction, or precise point positioning providing the coordinates (e.g., in two or three dimensions) of seeds or rows of plants for the field and a data processing system recording the coordinates of seeds or rows of plants, which can be referred to as as-planted data or planting map data (e.g., historic as-planted data from a planting that occurred earlier for the same field in the same growing season). As illustrated, the vehicle may be associated with a vehicle location-determining receiver 10 to estimate a position, heading or motion data of the vehicle, whereas the implement may be associated with an implement location-determining receiver 110 to estimate a position, heading or motion data of the implement 92. The as-planted data or planting map data can be stored as files on electronic storage media, non-volatile electronic random-access memory, optical disks, magnetic storage medium or otherwise for input to the user interface of the control system 11, or for wireless communication to the control system 11.

In one embodiment, one or more location-determining receivers (34, 66) determine the position of the implement in the field relative to as-planted seed data, seed density data, or both, where the as-planted seed data or seed density data may include any of the following: seed or plant row coordinates (e.g., two or three dimensions); position points that define linear or curved row segments; linear or quadratic equations that define linear or curved row segments; as-planted seed density data for corresponding linear or curved row segments through one or more fields; seed type and corresponding tolerance to concentration of fertilizer, corrosive components or salts that can dehydrate or damage plant tissue; seed coating (e.g., anti-corrosive, water soluble polymeric coating) of the planted seed and the resistance or tolerance of the seed coating to concentration of fertilizer, corrosive components or salts that can dehydrate or damage plant tissue.

In one configuration, the control system 11 or its vehicle guidance module 16 can guide the vehicle and the implement to track an implement path that has a target lateral offset (e.g., dynamically adjustable lateral offset versus vehicle or implement position) of the ground-engaging elements, openers or knives of the implement with respect to the as-planted data or planting map data.

Figure 13:
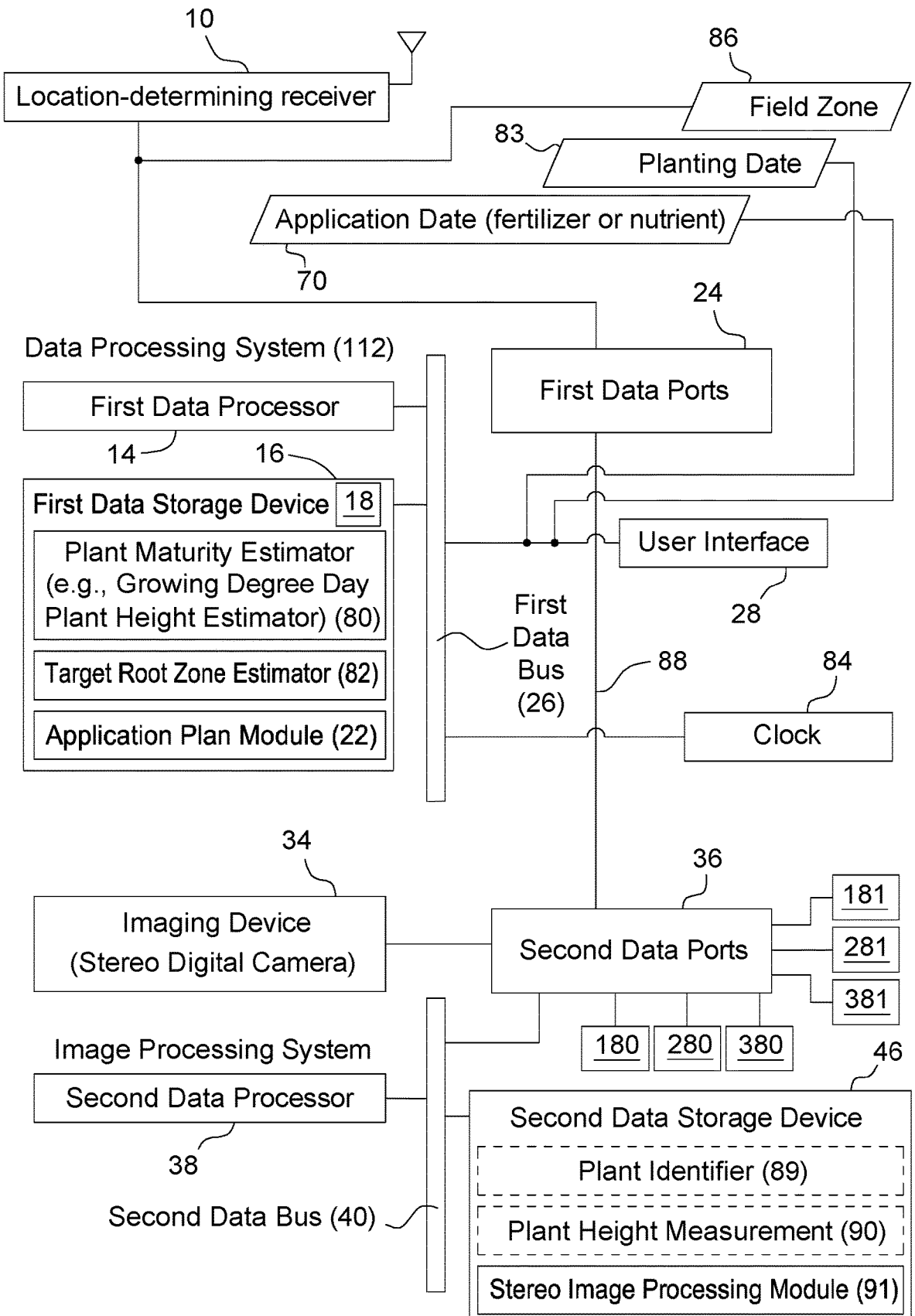
FIG. 13 is a block diagram of one embodiment of a system for applying fertilizer consistent with FIG. 12.

FIG. 13 is a block diagram of system for applying fertilizer consistent with FIG. 12. The system of FIG. 12 is similar to the system of FIG. 1, except the system of FIG. 12 further includes the following: (a) a plant maturity estimator 80 associated with the first data storage device 16 and first actuator 180; (b) first position sensor 181, second position sensor 281 and third position sensor 381; (c) a first actuator 180, a second actuator 280 and a third actuator 380; (d) a plant identifier module 89, plant height measurement module 90 and an imaging processing module 91 (e.g., stereo image processing module) associated with the second data storage device 146. The plant maturity estimator 80 may use one or more of the following data inputs to determine growing degree days, a plant maturity state, or a plant maturity indicator: (1) the planting date 83, such as planting date entered into the user interface 28 by an operator, (2) the present date or application date of fertilizer or nutrient, such as the application entered into the user interface 28 by an operator or provided by the clock 84, and (3) field zone data entered into the user interface 28 by the operator or extracted by reading of location data associated with the location-determining receiver 10.

In one embodiment, the image processing module 91 may comprise a stereo image processing module for determining a constellation of three dimensional coordinates that lie on or define the shape of an observed plant, plant row segment, or section of vegetation.

In another embodiment, the plant height measurement module 90 determines the observed height of a plant or plant row segment based on collected image data, the constellation of three dimensional coordinates, or other sensor data.

In an alternate embodiment, the optional plant identifier module 89 may provide a plant identifier, such as a plant species, a plant type, or plant variety, corn, maize, wheat, rice, oats, grain, soybeans, oilseed, fiber, or the like based on comparing an observed image collecting by the imaging device 34 to a reference image, with respect to an observed plant size (e.g., plant width or volume) and reference plant size, an observed leaf or vegetation shape and a reference leaf or vegetation shape, and an observed plant color and reference plant color. The plant maturity estimator 80 may use the plant identifier to estimate the plant maturity status consistent with reference plant maturity data stored in a look-up table, data base, chart or other data structure.

Figure 14:
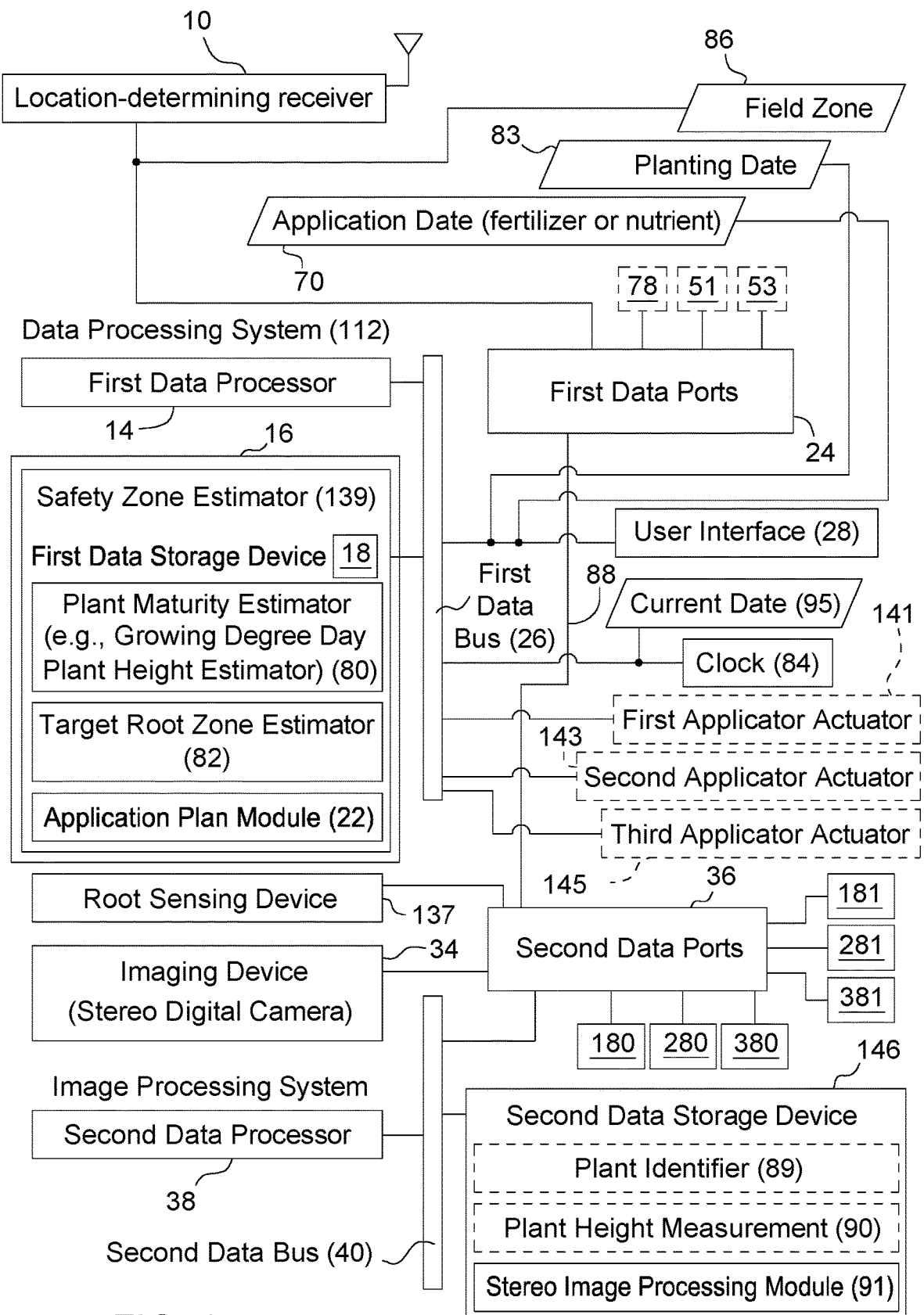
FIG. 14 is a block diagram of an alternate embodiment of system for applying fertilizer.

FIG. 14 is a block diagram of an alternate embodiment of system for applying fertilizer, nutrients or crop inputs. The system of FIG. 14 is similar to the system of FIG. 13, except the system of FIG. 14 further includes a first application actuator 141, a second application actuator 143, a third application actuator 145, an optional root sensing device 137, and a safety zone estimator 139. Like reference numbers indicate like elements or features. As illustrated in FIG. 14, the data processing system 112 further comprises a temperature sensor 78 for measuring air, ground or soil temperature; one or more environmental sensors 51 for measuring precipitation, accumulated daylight hours, soil moisture, soil parameters, or other agronomic parameters; and a wireless communications device 53 for communicating with environmental or agronomic data providers via a wireless network, such as a cellular, mesh or satellite wireless network.

In one embodiment, the root sensing device 137 measures all or portions an observed plant root zone. The observed plant root zone may be used alone or in conjunction with a plant maturity estimator 80 or target root zone estimator 82 to facilitate estimation of a root zone, safety zone, or extended safety zone. The root sensing device 137 may be used to estimate plant maturity based on a measured or detected root size, root dimensions, or root volume, which can be correlated to or indicative of plant maturity. In one example, the root sensing device 137 (e.g., ground-penetrating root-sensing device) may comprise any of the following: (a) an electrical impedance tomography imaging unit, (b) a ground-penetrating radar device or transceiver, and (c) a ground-penetrating radar configuration for measuring a size of underground roots of a plant.

In one configuration, a safety zone estimator 139 determines a distance between the estimated or measured extent of the root zone (N320 in FIG. 16) and where the fertilizer or nutrient application is to be targeted. If the ground-engaging nutrient knife 99 or applicator is too close to the roots of the plant, the roots may be chemically damaged or mechanically damaged. In one example, chemical damage of the roots can include burning by the concentration of fertilizer, whether by excessive acidity, alkalinity or residual salts in the soil around the roots of the plants. In another example, the physical damage of the roots can include mechanical damage from the nutrient knife 99 cutting, lacerating, shredding, scraping, bumping or other contact with the roots of the plants.

For corn or maize, the data processing system 112 can be used to control nutrient knives 99 in each corresponding row unit to apply crop inputs (e.g., nutrients or fertilizer): (a) outside of an inner safety zone N330 (in FIG. 16) or on an inner boundary N313 associated with an outer circumference of the inner safety zone N330, and/or (b) outside of (or bounded by) an outer safety zone N340 or on an outer boundary N315 associated with an outer circumference of the outer safety zone N340, which is well-suited for providing a safety margin to avoid damage to the roots of the rows of plants by the nutrient knives 99. In practice, there is some uncertainty as the actual limits of the root zone N320 of a corresponding plant, which may extend beyond the root boundary N311 to the inner boundary N313 or even the outer boundary N315. For example, the uncertainty may be associated with the error or tolerance in the position estimates of the location-determining receiver 10, which depends upon a differential correction signal or data message and carrier phase measurements of received satellite signals that are within range.

As illustrated in FIG. 16, at the root boundary N311, the inner safety zone N330 borders or surrounds the root zone N320 that is substantially circular or elliptical in a horizontal plane. The inner safety zone N330 (e.g., fixed safety) is substantially annular. Inward from the inner safety zone N330, the inner safety zone N330 is bounded by a root boundary N311 having inner radius (e.g., of approximately 3 centimeters) around a plant stalk N310 (e.g., stem, trunk or center point). Outward from the inner safety zone N330, the inner safety zone N330 is bounded by an inner boundary N313 having an outer radius (of approximately 6 centimeters) around a corresponding plant (stalk or center point), where the outer radius is greater than the inner radius of the inner safety zone N330.

In one embodiment, at an inner boundary N313 an outer safety zone N340 (e.g., adjusted safety zone) surrounds or borders an outer circumference the inner safety zone N330. The outer safety zone N340 is bounded by an outer boundary N315 having an outer radius. In one configuration, an aggregate safety zone refers to the combination of the inner safety zone N330 and the outer safety zone N340. If a crop input, such as nutrient or fertilizer, is applied with a given concentration on or outside the outer boundary N315 associated with the aggregate safety zone, then the plants generally will not sustain any material damage to the roots.

In one embodiment, the inner safety zone N330 may be a fixed region or fixed safety zone, or be subject to a fixed margin of error or tolerance. Meanwhile, the aggregate safety zone or outer safety zone N340 may comprise an adjustable safety zone, such as an adjusted safety zone of FIG. 16, that depends upon the concentration of the crop input (e.g., nutrient, fertilizer, chemical, pesticide or herbicide), the maturity of the plant, and other relevant agronomic factors, such as a root zone location quality factor, a Global Navigation Satellite System (GNSS) quality factor, a guidance system quality factor, a soil factor, and a fertilizer factor.

The radius, dimensions, or area of the outer safety zone N340 can be adjusted based on various factors. A root zone location quality factor is a measure or indicator of the confidence level in the size/location of the root zone of a plant, which can be derived from a crop model, a formula using measured plant attributes, or direct measurement of roots. For example, the safety zone estimator 139, plant maturity estimator 80, or target root zone estimator 82 may use a crop model to estimate a root zone location with a corresponding level of confidence (e.g., 90 percent confidence with a tolerance of plus or minus 2 centimeters in radius). In another example, the safety zone estimator 139 adds the above tolerance to an estimated or observed root radius to estimator a safety zone, such as an inner safety zone N330 (e.g., fixed safety zone) or generally annular safety zone about a plant. In yet another example, the safety zone estimator 139 adds the above tolerance (e.g., 2 centimeters in radius) to an existing inner safety zone N330 (e.g., fixed safety zone) (e.g., 3 centimeters in radius) to yield a greater outer safety zone N340 (e.g., adjusted safety zone). The outer safety zone N340 may be referred to as an adjustable safety zone because the outer safety zone N340 (e.g., adjusted safety zone) has a radius, dimension or area that is adjusted based on factors for evaluating the precision and reliability of plant positions with respect to the vehicle, implement or nutrient knives 99. The outer safety zone N340 is located outward from the inner safety zone N330 (e.g., fixed safety zone), where both the inner safety zone and the outer safety zone are generally annular or substantially ring-shaped.

A satellite navigation quality factor (e.g., Global Navigation Satellite System (GNSS)) may be derived from parameters such as theoretical limits to accuracy, satellite constellation, dilution of precision, or other factors. The location-determining receiver 10 may comprise a quality module that provides the satellite navigation quality factor to the data processing system.

A guidance system quality factor is related to the ability of each applicator or nutrient knife 99 associated with the implement to follow a prescribed path in the ground to avoid physical damage or chemical damage to the roots of the rows of plants consistent with a safety zone, such as an inner safety N330 zone (e.g., fixed safety zone), an outer safety zone N340 (e.g., an adjusted or dynamically adjustable safety zone). The guidance system quality factor may be impacted by the ground speed of the applicator or nutrient knife 99, soil properties, such as clay content and moisture content, the geometry of the steering system of the work machine or tractor with respect to the implement, among other things. The first data processor 14 or the application plan module 22 may provide or estimate a guidance system quality factor.

A soil factor, such as an existing soil acidity/alkalinity (e.g., pH) and salinity may affect the likelihood of chemical root damage for a given fertilizer application, path plan of nutrient knife 99 or knives, consistent with one or more safety zones. The data processing system 112 may receive or obtain soil surveys or geo-referenced soil sample parameters versus position (e.g., in two or three-dimensional coordinates) via a user interface 28 or otherwise.

In an alternate embodiment, the data processing system 112 is associated with a soil sensor that penetrates or contacts the soil to estimate any of the following soil parameters: soil moisture, soil acidity, soil alkalinity, soil pH, and soil salinity.

A fertilizer factor, such as the concentration of nitrogen, phosphorus and potassium and the chemical or compound form/biological availability of the fertilizer or nutrient may affect the likelihood of chemical root damage.

In one embodiment, the first actuator 180 controls a first lateral position of a corresponding first nutrient knife 99 or set of first nutrient knives 99, where the first position sensor 181 measures or provides a measurement to estimate the first lateral position; the second actuator 280 controls a second lateral position of a corresponding second nutrient knife 99 or set of second nutrient knives 99, where the second position sensor 281 measures or provides a measurement to estimate the second lateral position; the third actuator 380 controls a third lateral position of a corresponding third nutrient knife 99 or set of nutrient knives 99, where the third position sensor 381 measures or provides a measurement to estimate the third lateral position. As shown in FIG. 12, each set of one or more (e.g., five) nutrient knives 99 can be laterally adjusted simultaneously and independently of other sets of nutrient knives 99. The data processing system 112 can control the set of one or more nutrient knives 99 to follow planned paths with predefined spacing or separation with respect to rows of plants or individual plants. Further, the data processing system 112 can control the set of one or more nutrient knives 99 to follow the planned paths, such as generally linear paths (e.g., N360 in FIG. 16) or generally linear paths with arcs (e.g., N350 in FIG. 16) about root zones (e.g., N320) or plant stems or stalks (e.g., N310)) with predefined spacing or separation with respect to plants and consistent with an inner safety zone, an outer safety zone, or both.

In an alternate embodiment, the implement includes an optional first applicator actuator 141, an optional second applicator actuator 143 and an optional third applicator actuator 145, which are indicated by dashed lines in FIG. 14. In the alternate embodiment, each optional applicator actuator may be used to adjust a depth of a nutrient outlet associated with corresponding nutrient knives.

In another alternate embodiment, the applicator (141, 143, 145) for each row unit comprises the combination of a nutrient knife 99 for below ground applications of nutrients and a sprayer nozzle for above ground applications of nutrients of nutrients. Further, each optional applicator actuator (141, 143, 145) may be used to selectively activate one or more of the following for each equipped row unit: (a) the nutrient knife 99 outlet of nutrient from the nutrient knife 99 for below ground application, (b) the nozzle outlet of nutrient for above ground applications, where the nutrient knife outlet (of nutrient knife 99) and nozzle outlet can be activated at a start time and an end time associated with proximity to each plant, root zone, plant stem or plant stalk to limit the amount of fertilizer applied and maximize the impact of the fertilizer on plant growth and yield.

In yet another alternate embodiment, each optional applicator actuator (141, 143, 145) comprises an electrohydraulic valve that is activated to open, close, or regulate a valve associated with the nutrient knife outlet of the nutrient knife 99, the nozzle outlet or both. The selectively timed and limited application of such nutrients has the potential to reduce runoff or indirect delivery of nutrients to watersheds to reduce or ameliorate potential algae growth and potential environmental hypoxia and in lakes, rivers and oceans.

Figure 15:
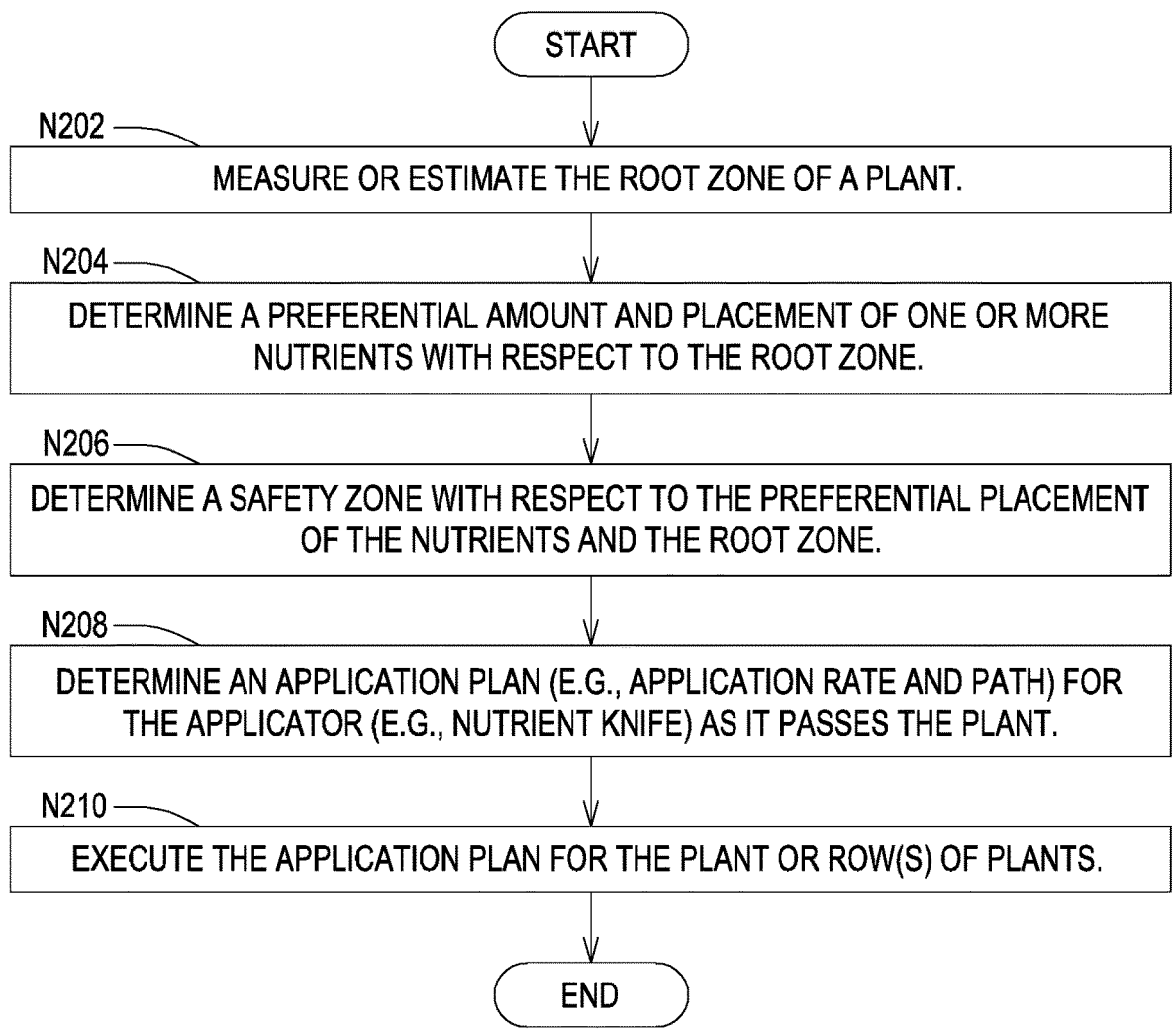
FIG. 15 is a flow chart of one embodiment of a method for treating or applying nutrients to plants.

FIG. 15 is a flow chart of one embodiment of a method for treating or applying nutrients to plants. The method of FIG. 15 begins in step N202.

In step N202, the target root zone estimator 82 or plant maturity estimator 80 estimates or measures the extent or size and location of a plant root zone N320. For example, the location of a center point N357 of the root zone N320 may be associated with two or three-dimensional position coordinates or center point N357 of a plant stalk N310 or stem, whereas the size of the root zone may be defined by a radius about the location or center point N357. Further, the root zone N320 may be defined in accordance with or supplemented with one or more safety zones, such as an inner safety zone N330 (e.g., fixed safety zone) and an outer safety zone N340 (e.g., an adjustable safety zone). Step N202 may be supported by the first data processor 14, the second data processor 38, or both.

Although the root zone N320 may be defined in two dimensions, as illustrated in FIG. 16, in an alternate embodiment, the root zone may be defined in three dimensions or by its volume. In some examples, the size or radius of the root zone N320 is informed by genetic root zone architecture for the plant species and plant variety that has been planted, and above ground measured plant parameters, such as plant height, plant width, or both.

In one embodiment, the plant maturity estimator 80 or target root zone estimator 82 estimates the growth state or the plant maturity is based on growing degree days derived from temperature data for the geographic area associated with the plant, the planting date, the current date and the crop type of the plant. In accordance with one estimation process, the plant maturity estimator 80 or target root zone estimator 82 estimates the growth state or plant maturity based on a growth model that uses a historic mean, average or median precipitation for the location of the plant, the planting date, the current date and the crop type of the plant. The planting date may be entered by a user via the user interface 28, whereas the current date 95 is automatically determined by a clock 84 or another chronometer. In accordance with another estimation process, the growth state or plant maturity is based on observed rainfall or precipitation for the field or region associated with the plant, which is inputted from a user at the user interface 28, wirelessly received by a wireless communications device 53 coupled to the first data ports, or provided by sensor data from one or more environmental sensors 51.

In certain configurations, a root sensing device 137 or imaging device 34 can collect sensor data to verity the estimated location and size of the target root zone N320. For example, the imaging device 34 is adapted to collect stereo image data on the plant to evaluate a plant size or plant height to verify the determined growth state or maturity state for the plant. The plant maturity estimator 80 or the target root zone estimator 82 can adjust the determined growth state or maturity state for the plant based on the collected stereo image data predominating over the derived growing degree days. In another example, the imaging device 34 is adapted to collect observed plant height data on the plant to verify the determined growth state of maturity state for the plant. In one embodiment, the plant maturity estimator 80 or target root zone estimator 82 adjusts the determined growth state or maturity state for the plant based on the observed plant height predominating of the derived growing degree days.

In an alternate embodiment of step N202, the plant maturity estimator 80 or target root zone estimator 82 estimates or determines a growth state or maturity state of a plant based on a planting date, accumulated growing degree days since the planting date, and the crop type of the plant. In some configurations, the calculation of growing degree days requires a temperature sensor 78 for the temperature measurements and a clock 84 (e.g., for providing the time and/or current date 95), or the user may enter accumulated growing degree days data via the user interface 28, or the data processing system 112 may receive accumulated or derived growing degree days from a third party data provider via a wireless communications device 53 that communicates over a wireless communications network, such as a cellular, mesh, or satellite network. The temperature sensor 78 may be coupled to the first data ports 24, or second data ports 36, of the data processing system 112.

In step N204, the safety zone estimator 139, the application plan module 22 or the first data processor 14 determines a preferential amount and placement of one or more nutrients with respect to the measured or estimated root zone N320. Step N204 may be carried out in accordance with various techniques, which may be applied separately, or cumulatively.

Under a first technique, the safety zone estimator 139, the application plan module 22 or the first data processor 14 determines the amount and placement of one or more nutrients with respect to the measured or estimated root zone N320 or safety zone to accomplish one or more of the following objectives: (a) to avoid damage to the plants, (b) to maximize yield associated with the plants or crop, and (c) to minimize the application of nutrients or crop inputs required to maximize yield. For example, in accordance with step N204 the distribution pattern comprises a generally linear strip or an arc that intercepts a safety zone outward from a root zone.

Under a second technique, the application plan module 22 or the first data processor 14 determines that the plant has a corresponding yield goal of 5 milli-bushels (i.e., $5 \times 10^{-3}$ bushels) and a nitrogen budget of 1.5 units of nitrogen/bushel or 7.5 milli-units of nitrogen for the plant. Further, the application plan module or the first data processor 14 allocates a portion of the fertilizer budget or nitrogen budget, which may be applied as a function of milliliters of a liquid fertilizer by the nutrient knife 99 below ground near a base of the plant and its root zone, but not so close to the root zone to physically damage, cut, or abrade the root or root zone of the corresponding plant.

Under a third technique, the application plan module 22 or the data processor 14 determines control signals or data messages for one or more lateral position actuators (180, 280, 380) associated with the applicator or nutrient knife 99 and for one or more flow-control applicator actuators (141, 143, 145) to apply the fertilizer in the soil in a generally linear band (e.g., N360) or arc (e.g., N355) of a certain length (e.g., 15-centimeter-long band or arc), as close as allowed to the plant consistent with the corresponding root zone N320 and associated safety zone(s) (e.g., N330, N340).

Under a fourth technique, the data processor 14 or application plan module 22 determines control signals or data messages for one or more lateral position actuators (180, 280, 380) associated with the applicator or nutrient knife 99 and for one or more depth-control applicator actuators (141, 143, 145) to apply the fertilizer in the soil in a band or arc to a depth (e.g., 10 centimeters) that is chosen such that the fertilizer migrates or diffuses down and over the roots or so the roots grow down and over to the migrated or diffused fertilizer.

Under a fifth technique, the data processor 14 or application plan module 22 determines control signals or data messages for one or more actuators (180, 280, 380) associated with the applicator or nutrient knife 99 to apply or manage fertilizer or other crop inputs in the root zone based on historical rainfall, forecasted rainfall, irrigation plans, and/or soil moisture measurements or surveys of the field with the plants or crop.

Under a sixth technique, the data processor 14 or application plan module 22 determines control signals or data messages for one or more actuators (180, 280, 380) to adjust a lateral offset of a distribution pattern (e.g., a strip or arc that intercepts a safety zone outward from a root zone) of a crop input or nutrient from (a nutrient knife 99 assembly of) one or more nutrient knives 99 based on the size, diameter or radius of a root zone N320 and safety zone (e.g., N330 or N340) about the root zone, where each of the one or more nutrient knives tracks 99 a path outside of the root zone N320.

In step N206, a data processor 14 or safety zone estimator 139 determines a safety zone (e.g., N330 or N340) about the estimated or measured root zone (e.g. N320). The data processor 14 or safety zone estimator 139 estimates the safety zone (e.g., N320) about each plant in a row in accordance with techniques, which may be applied separately or cumulatively.

Under a first technique, the inner safety zone N330 is initially determined with as a fixed safety zone about the plant root zone N330, or radius about the plant stalk N310, stem or center point N357, where the inner safety zone N330 is selected to avoid mechanical or physical damage to the roots of the plant, chemical damage to the roots of the plant, or both.

Under a second technique, the data processor 14 or safety zone estimator 139 adjusts or determines the outer safety zone N340 (e.g., adjusted safety zone) based on the accuracy or tolerance of the reliable position estimates or location estimates of the location-determining receiver 10. For instance, if the location-determining receiver 10 comprises a Global Navigation Satellite System (GNSS) satellite receiver that is operating with precise point positioning and associated correction signal, the accuracy may be equal to or better than a particular accuracy rating (e.g., tolerance of plus or minus approximately 3 centimeters); hence, the outer safety zone N340 (e.g., adjusted safety zone) has its associated radius is added to the inner safety zone N330 (e.g., fixed safety zone). Similarly, if the location-determining receiver 10 comprises a GNSS satellite receiver that is operating on a real-time kinematic (RTK) mode with one or more reference base stations providing local differential correction signals, the accuracy may be equal to or better than the particular accuracy rating (e.g., tolerance of plus or minus approximately 2.5 centimeters); hence, the outer safety zone N340 (e.g., adjusted safety zone) has its associated radius is added to the inner safety zone N330 (e.g., fixed safety zone).

Under a third technique, the data processor 14 or safety zone estimator 139 adjusts or determines the outer safety zone N340 (e.g., adjusted safety zone) to extend an additional radial length (e.g., approximately three centimeters in radius outward from the root zone or an inner safety zone) as outer safety zone N340 (e.g., adjusted safety zone) to account for implement guidance error (e.g., tolerance of plus or minus approximately three centimeters).

Under a fourth technique, the data processor 14 or safety zone estimator 139 adjusts or determines the outer safety zone N340 (e.g., adjusted safety zone) to extend an additional radial length (e.g., approximately six centimeters in radius outward from the root zone or an inner safety zone) as outer safety zone N340 (e.g., adjusted safety zone) to account for implement guidance error (e.g., tolerance of plus or minus approximately three centimeters) and GNSS receiver accuracy (e.g., tolerance of approximately three centimeters).

Under a fifth technique, in one embodiment the aggregate safety zone (N330, N340) comprises a generally annular zone outward from the root zone of a corresponding plant in the row.

Under a sixth technique, in another embodiment the safety zone comprises an outer safety zone N340 (e.g., adjusted safety zone) that comprises a generally annular zone that is adjusted based on the growth stage or maturity of plants with the row and concentration of the nutrients.

In step N208, the first data processor 14 or the application plan module 22 determines the route or path plan (e.g., N360 or N350) of the nutrient knife 99 or set of nutrient knives for each row or set of rows consistent with the estimate root zone and safety zone (e.g., inner safety zone N330, outer safety zone N340 or both). For example, the first data processor 14 or the application plan module 22 determines the path plan of the nutrient knife 99 or nutrient knives and corresponding activation and deactivation times of for the nutrient outlet of each nutrient knife 99 to align or coincide with one or more of the following: (a) plant stalk, plant stem N310 or center point N357 of each plant in a row, (b) a location, position or geographic coordinates of the location-determining receiver 10 on the tractor or on the implement associated with a plant stalk, plant stem or center point N357 of each plant, or (c) a location, position or geographic coordinates of an application start point (N352 or N362) and an application end point (N354 or N364) for a generally linear path plan N360 or a linear path plan with an arc N355 (e.g., path plan with arc deviation N350) and associated center point N357 of the arc N355 coincident with the stem location, stalk location N310 or center point N357 of plant in a plant row. The path plan for each row or applicator route has an application start point (N352 or N362) and an application end point (N354 or N364), where the outlet of the nutrient knife 99 ejects or emits nutrient or fertilizer as the nutrient knife 99 traverses the path plan between the application start point (N352 or N362) and the application end point (N354 or N364). Further depending upon the trajectory responsiveness or lateral responsiveness of the nutrient knife 99 of each row unit along with the corresponding ground speed of the vehicle, tractor or implement with the nutrient knife 99 or knives, the data processor 14 or the application plan module 22 may elect to execute general linear path or application route, as opposed to an application route or path plan with linear segments and an arc N355 about each plant or its root zone.

In some examples, the data processor 14 or application plan module 22 controls multiple nutrient knives 99 or sets of nutrient knives 99 to move laterally together in unison to track parallel substantially linear paths (N360) or parallel linear path segments interrupted by arcs (N350) that diverge outward from the respective root zones. In addition, the data processor 14 or application plan module 22 can control sets of nutrient knives 99 to move laterally and vertically together. In these cases, the individual row lateral displacements and depths may need to be resolved while considering the following parameters: (a) application outside the lateral safety zone, (b) average lateral distance from an adjacent or closest plant row, (c) minimum depth of the nutrient knife 99, (d) maximum depth of the nutrient knife 99, and (e) average depth of the nutrient knife 99.

In step N210, the first data processor 14 or application plan module 22 facilitates movement of the applicator and nutrient knives 99 of the row units via the lateral actuators (180, 280, 380) along one of the application routes or path plans, such as those application routes illustrated in FIG. 16. Further, the first data processor 14 or application module facilitates dispensing or emission of nutrients or fertilizer between the application start point (N352 or N362) and the application end point (N354 or N364) by activating or regulating the flow-control applicator actuators (141, 143, 145), such as electrohydraulic valves in the lines associated with the nutrient outlets at the respective nutrient knives 99.

Step N210 may be carried out in accordance with various procedures that may be implemented separately or cumulatively.

Under a first procedure for carrying out step N210, the first data processor 14 or lateral position actuator (180, 280, 380) adjusts a lateral offset of a distribution pattern of a crop input or nutrient from at least one nutrient knife 99 of nutrient knife 99 assembly based on the size, diameter or radius of the root zone and safety zone about the root zone N320, where the least one nutrient knife 99 tracks a path outside of the root zone N320 to avoid mechanical damage or chemical damage to the root or plant.

Under a second procedure, the first data processor 14 commands or instructs:(a) an actuator (141, 143, 145) (e.g., an electrohydraulic valve) associated with the nutrient knife 99 assembly to activate the distribution of the crop input or nutrient from the at least one ground-engaging nutrient knife 99 from an application start point (N352 or N362) to an application end point (N354 or N364) lying along a substantially linear path that intercepts safety zone outward from a root zone about each stalk within a row of plants, and (b) an actuator associated with the lateral position of the at least one ground-engaging nutrient knife 99 to direct the at least one nutrient knife 99 to track the linear row path that intercepts the safety zone outward from the root zone about each stalk within a row of plants based on feedback or sensor data from position sensor (181, 281, 381) (e.g., lateral position sensor).

Under a third procedure, the first data processor 14 commands or instructs: (a) an actuator (141, 143, 145) (e.g., an electrohydraulic valve) associated with the nutrient knife 99 assembly to activate the distribution of the crop input or nutrient from the at least one ground-engaging nutrient knife 99 from an application start point (N352 or N362) to an application end point (N354 or N364) lying along a substantially linear row path with an arc N355 that intercepts a safety zone (e.g., outer safety zone N340) outward from a root zone N320 about each stalk N310 within a row of plants, and (b) an actuator (180, 280, 380) associated with the lateral position of the at least one ground-engaging nutrient knife 99 to direct the at least nutrient knife 99 to track an arc N355 that extends outward, with respect to each corresponding plant with the row, from a substantially linear track that is parallel to a row of plants and outside of the root zones N320 of the row of plants.

Under a fourth procedure, the data processor 14 or application plan module 22 the substantially linear row path (N350 or N360) is associated with a corresponding application start point (N3521 or N362) and a corresponding application end point (N354 or N364) for each plant in the row, where the application or distribution of the nutrient is when the ground-engaging nutrient knife traverses the substantially linear path, or the substantially linear path with an arc N355, or arc deviation, between the application start point (N352 or N362) and the application end point (N354 or N364).

Although the examples in the disclosure and method of FIG. 15 have focused on nutrient and fertilizer application, similar configurations can be used to dispense or distribute other chemicals, compounds, or crop inputs, such as fungicides, herbicides, insecticides, nematicides, pesticides, and miticides.

FIG. 16 is a plan view of a nutrient knife 99 that tracks one of two possible path plans (N350 or N360) or routes plan for treating or applying nutrients to plants. A stalk N310, stem or plant center point N357 is part of a row of plants or crops, where the stalk N310, stem or plant center point is associated with a location, position or coordinates estimated by a location-determining receiver 10. A root zone N320 has a radius about the stalk N310, stem or plant center point N357, where the target root zone estimator 82, or plant maturity estimator 80, or first data processor 14 estimate the root zone. Alternately, the root sensing device 137 estimates the root zone for one or more plants. Imaging data or the plant may supplement the data or model information association with the plant maturity estimator 80 to estimate a size or radius of the root zone about the stalk, stem or plant center point.

In FIG. 16, an inner safety zone N330 (e.g., fixed safety zone) is located outward from the root zone N320 and the stalk N310, stem or center point N357 of the plant. The outer circumference or root boundary N311 of the root zone N320 is coincident or coextensive with an inner circumference or inner boundary of the inner safety zone N330. As illustrated, the inner safety zone N330 has a substantially annular area. An outer circumference or inner boundary N313 of the inner safety zone is coincident or coextensive with an inner circumference or inner boundary of the outer safety zone N340 (e.g., adjusted safety zone).

In one embodiment, an outer circumference or outer boundary N315 of the outer safety zone N340 or outer safety zone N340 (e.g., adjusted safety zone) can intercept a first path N360 or a second path N350. The first path N360 comprises a generally linear path or route of a nutrient knife 99 along a row of plants. The second path N350 comprises a pair of generally linear path segments N317 that are interconnected or interrupted by an arc N355 for the nutrient knife 99 to follow along a row of plants. In accordance with the second path N350, the nutrient knife 99 follows an arc N355, which can be described as an arc excursion or deviation outward away from the plant stalk N310, stem or center point N357, where the arc N355 is coextensive with a portion of the outer circumference or outer boundary N315 of the outer safety zone N340 (e.g., adjusted safety zone The first path N360 or the second path N350 represent alternative paths for the nutrient knife 99 traversing a plant row; the first path N360, which is generally or substantially linear, is typically favored for higher speed applications or distribution of fertilizer equal to or greater than a certain ground speed threshold of the implement or tractor pulling the implement, whereas the second path N350 can be used as lower speeds lesser than the certain ground speed threshold. The second path N350 potentially can provide higher concentration of nutrients or fertilizer around the root zone N320 because the arc has a center point N357 that is aligned with a center point N357 of the stalk N310, stem or center point of the plant and that is aligned with the root zone N320.

For the first path N360 or the second path N350 of each row unit, the first data processor 14 or application plan module 22 establishes an application start point (N362 or N352) and an application end point (N364 or N354), between which nutrient or fertilizer is distributed. The location-determining receiver 10 facilitates estimation of the application start point (N352 or N362) and application end point (N354 or N364) for each row unit. Meanwhile, the first data processor 14 or application plan module 22 can generate control signals or control data messages to activate the actuators (141, 143, 145) or electrohydraulic valves to activate, deactivate and regulate the flow of nutrients or fertilizer from the nutrient outlet of the nutrient knife 99 of each plant row, consistent with the applicable application start point (N352 or N362) and the applicable application end point (N354 or N364).

The radial lengths that appear in FIG. 16 are merely provided for illustrative purposes and do not limit the root zone N320, the inner safety zone N330 or the outer safety zone N340 to any particular radial dimensions or radial lengths, such as five centimeters, two centimeters or five centimeters, respectively.

The system disclosed in this document is well-suited for selecting or controlling vertical position of active nozzles to provide desired application of crop input to one or more target zones on the soil, and/or vegetation. Further, the system can adjust the spray pattern for each crop row independently and dynamically to select a different spray pattern for each time interval and for each respective crop row segment of any crop row or set of crop rows. The system can be configured to adjust the spray patterns for each crop row segment based on observed or measured lateral spacing within each row to compensate for as-planted variation or error in crop row spacing, such as variation associated with manual driving during planting or from use of satellite navigation service or satellite navigation receivers that do not feature the latest technology in precise positioning.

While the disclosure has been described in detail in the drawings and foregoing description, the description shall be considered as exemplary and illustrative, rather than restrictive of the scope of protection set forth in the claims. Various illustrative embodiments have been shown and described in this document, such that any changes, variants and modifications that come within the spirit of the disclosure will fall within the scope of the disclosure and its associated claims.

The following is claimed:

1. A method for treating or applying nutrients to plants, the method comprising:

determining a growth state or maturity state of a plant based on a planting date, a current date and the crop type of the plant;

estimating a size, diameter or radius of a root zone of the plant based on the determined growth state or maturity state;

adjusting a lateral offset of a distribution pattern of a crop input or nutrient from at least one nutrient knife of nutrient knife assembly based on the size, diameter or radius of the root zone and safety zone about the root zone, where the at least one nutrient knife tracks a path outside of the root zone; and commanding or instructing an actuator associated with the nutrient knife assembly to activate the distribution of the crop input or nutrient from the at least one ground-engaging nutrient knife directed along a linear row path with an arc deviation that intercepts a safety zone outward from a root zone about each stalk within a row of plants, where the arc deviation extends outward with respect to each corresponding plant with the row.

2. The method according to claim 1 wherein the distribution pattern comprises a strip or arc that intercepts a safety zone outward from a root zone.

3. The method according to claim 1 wherein the growth state or the plant maturity is based on growing degree days derived from temperature data for the geographic area associated with the plant, the planting date, the current date and the crop type of the plant, where the derived growing degree days are accumulated between the planting date and the current date.

4. The method according to claim 3 further comprising:

collecting stereo image data on the plant to evaluate a plant size or plant height to verify the determined growth state or maturity state for the plant;

adjusting the determined growth state or maturity state for the plant based on the collected stereo image data predominating over the derived growing degree days.

5. The method according to claim 3 further comprising:

collecting observed plant height data on the plant to verify the determined growth state of maturity state for the plant;

adjusting the determined growth state or maturity state for the plant based on the observed plant height predominating of the derived growing degree days.

6. The method according to claim 1 wherein the growth state or plant maturity is based on a growth model that uses a historic mean, average or median precipitation for the location of the plant, the planting date, the current date and the crop type of the plant.

7. The method according to claim 6 wherein the growth state or plant maturity is based on observed rainfall or precipitation for the field or region associated with the plant.

8. The method according to claim 1 wherein the growth state or plant maturity is further based on root size measurements of a root sensing device.

9. The method according to claim 1 further comprising:

commanding or instructing an actuator associated with the nutrient knife assembly to activate the distribution of the crop input or nutrient from the at least one ground-engaging nutrient knife directed along a linear row path that intercepts safety zone outward from a root zone about each stalk within a row of plants.

10. The method according to claim 9 wherein the safety zone comprises a generally annular zone outward from the root zone of a corresponding plant in the row.

11. The method according to claim 9 wherein the safety zone comprises an outer safety zone that comprises a generally annular zone that is adjusted based on the growth stage or maturity of plants with the row and concentration of the nutrients.

12. The method according to claim 9 wherein the linear row path is associated with a corresponding application start point and a corresponding application end point for each plant in the row, where the application or distribution of the nutrient is active when the ground-engaging nutrient knife traverses the linear row path.

13. The method according to claim 1 wherein the safety zone comprises a generally annular zone outward from the root zone of a corresponding plant in the row.

14. The method according to claim 1 wherein the safety zone comprises an outer safety zone that comprises a generally annular zone that is adjusted based on the growth stage or maturity of plants with the row and concentration of the nutrients.

15. The method according to claim 1 wherein the safety zone comprises a generally annular zone outward from the root zone of a corresponding plant in the row.

16. The method according to claim 1 wherein the safety zone comprises an outer safety zone that comprises a generally annular zone that is adjusted based on the growth stage or maturity of plants with the row and concentration of the nutrients.

17. A method for treating or applying nutrients to plants, the method comprising:

determining a growth state or maturity state of a plant based on a planting date, accumulated growing degree days since the planting date, and the crop type of the plant;

estimating a size, diameter or radius of a root zone of the plant based on the determined growth state or maturity state;

adjusting a lateral offset of a distribution pattern of a crop input or nutrient from at least one nutrient knife of nutrient knife assembly based on the size, diameter or radius of the root zone and safety zone about the root zone, where the at least one nutrient knife tracks a path outside of the root zone; and commanding or instructing an actuator associated with the nutrient knife assembly to activate the distribution of the crop input or nutrient from the at least one ground-engaging nutrient knife directed along a linear row path that intercepts the safety zone outward from a root zone about each stalk within a row of plants, wherein the linear row path is associated with a corresponding application start point and a corresponding application end point for each plant in the row, where the application or distribution of the nutrient is active when the ground-engaging nutrient knife traverses a path plan between the application start point and the application end point.

18. The method according to claim 17 wherein the safety zone comprises a generally annular zone outward from the root zone of a corresponding plant in the row.

19. The method according to claim 17 wherein the safety zone comprises an outer safety zone that comprises a generally annular zone that is adjusted based on the growth stage or maturity of plants with the row and concentration of the nutrients.

20. The method according to claim 17 further comprising:
commanding or instructing an actuator associated with the nutrient knife assembly to activate the distribution of the crop input or nutrient from the at least one ground-engaging nutrient knife directed along a linear row path with an arc deviation that intercepts a safety zone outward from a root zone about each stalk within a row of plants, where the arc extends outward with respect to each corresponding plant with the row.

21. The method according to claim 20 wherein the safety zone comprises a generally annular zone outward from the root zone of a corresponding plant in the row.

22. The method according to claim 20 wherein the safety zone comprises an outer safety zone that comprises a generally annular zone that is adjusted based on the growth stage or maturity of plants with the row and concentration of the nutrients.

23. The method according to claim 20 wherein the safety zone comprises a generally annular zone outward from the root zone of a corresponding plant in the row.

24. The method according to claim 20 wherein the safety zone comprises an outer safety zone that comprises a generally annular zone that is adjusted based on the growth stage or maturity of plants with the row and concentration of the nutrients.

25. A method for treating or applying nutrients to plants, the method comprising:
determining a growth state or maturity state of a plant based on a measured root size via a ground-penetrating root-sensing device;
estimating a size, diameter or radius of a root zone of the plant based on the determined growth state or maturity state;
adjusting a lateral offset of a distribution pattern of a crop input or nutrient from at least one nutrient knife of nutrient knife assembly based on the size, diameter or radius of the root zone and safety zone about the root zone, where the at least one nutrient knife tracks a path outside of the root zone; and
commanding or instructing an actuator associated with the nutrient knife assembly to activate the distribution of the crop input or nutrient from the at least one ground-engaging nutrient knife directed along a linear row path that intercepts the safety zone outward from a root zone about each stalk within a row of plants, wherein the linear row path is associated with a corresponding application start point and a corresponding application end point for each plant in the row, where the application or distribution of the nutrient is active when the ground-engaging nutrient knife traverses a path plan between the application start point and the application end point.

26. A method for treating or applying nutrients to plants, the method comprising:
determining a growth state or maturity state of a plant based on a planting date, a current date and the crop type of the plant, wherein the growth state or the plant maturity is based on growing degree days derived from temperature data for a geographic area associated with the plant, the planting date, the current date and the crop type of the plant, where the derived growing degree days are accumulated between the planting date and the current date;
estimating a size, diameter or radius of a root zone of the plant based on the determined growth state or maturity state;
adjusting a lateral offset of a distribution pattern of a crop input or nutrient from at least one nutrient knife of nutrient knife assembly based on the size, diameter or radius of the root zone and safety zone about the root zone, where the at least one nutrient knife tracks a path outside of the root zone;
collecting stereo image data on the plant to evaluate a plant size or plant height to verify the determined growth state or maturity state for the plant; and
adjusting the determined growth state or maturity state for the plant based on the collected stereo image data predominating over the derived growing degree days.

* * * * *